United States Patent
Saint-Remy

(10) Patent No.: US 10,899,795 B2
(45) Date of Patent: Jan. 26, 2021

(54) MODIFIED EPITOPES FOR BOOSTING CD4+ T-CELL RESPONSES

(71) Applicants: Katholieke Universiteit Leuven, Leuven (BE); Life Sciences Research Partners VZW, Leuven (BE)

(72) Inventor: Jean-Marie Saint-Remy, Grez-Doiceau (BE)

(73) Assignees: LIFE SCIENCES RESEARCH PARTNERS VZW, Leuven (BE); KATHOLIEKE UNIVERSITEIT LEUVEN, Leuven (BE)

(*) Notice: Subject to any disclaimer, the term of this patent is extended or adjusted under 35 U.S.C. 154(b) by 269 days.

(21) Appl. No.: 14/375,324

(22) PCT Filed: Jan. 30, 2013

(86) PCT No.: PCT/BE2013/000006
§ 371 (c)(1),
(2) Date: Jul. 29, 2014

(87) PCT Pub. No.: WO2013/113076
PCT Pub. Date: Aug. 8, 2013

(65) Prior Publication Data
US 2014/0370044 A1  Dec. 18, 2014

Related U.S. Application Data

(60) Provisional application No. 61/592,404, filed on Jan. 30, 2012.

(30) Foreign Application Priority Data

Jan. 30, 2012 (GB) .................................. 1201511.1

(51) Int. Cl.
| | |
|---|---|
| *A61K 38/10* | (2006.01) |
| *A61K 38/16* | (2006.01) |
| *A61K 39/00* | (2006.01) |
| *C12N 5/0783* | (2010.01) |
| *C07K 7/08* | (2006.01) |
| *A61K 39/04* | (2006.01) |
| *A61K 39/35* | (2006.01) |
| *C07K 14/47* | (2006.01) |
| *C07K 14/435* | (2006.01) |
| *A61K 35/17* | (2015.01) |
| *A61K 38/17* | (2006.01) |
| *A61K 39/145* | (2006.01) |

(52) U.S. Cl.
CPC .............. *C07K 7/08* (2013.01); *A61K 35/17* (2013.01); *A61K 39/04* (2013.01); *A61K 39/35* (2013.01); *C07K 14/43531* (2013.01); *C07K 14/4713* (2013.01); *C12N 5/0637* (2013.01); *A61K 38/1709* (2013.01); *A61K 38/1767* (2013.01); *A61K 39/0011* (2013.01); *A61K 39/145* (2013.01); *A61K 2039/572* (2013.01); *C12N 2501/05* (2013.01); *C12N 2760/16122* (2013.01)

(58) Field of Classification Search
None
See application file for complete search history.

(56) References Cited

U.S. PATENT DOCUMENTS

| | | | |
|---|---|---|---|
| 4,599,231 A | 7/1986 | Milich et al. | |
| 4,886,782 A | 12/1989 | Good et al. | |
| 5,433,948 A | 7/1995 | Thomas et al. | |
| 5,552,142 A | 9/1996 | Thomas et al. | |
| 5,589,175 A | 12/1996 | Vahlne et al. | |
| 5,633,234 A | 5/1997 | August et al. | |
| 5,736,142 A * | 4/1998 | Sette ........................ | C07K 7/08 424/184.1 |
| 5,770,202 A | 6/1998 | Thomas et al. | |
| 5,773,002 A | 6/1998 | Thomas et al. | |
| 5,863,528 A | 1/1999 | Hawley et al. | |
| 6,399,383 B1 | 6/2002 | Apt et al. | |
| 6,602,509 B1 | 8/2003 | Saint-Remy et al. | |
| 6,656,471 B1 | 12/2003 | Sastry et al. | |
| 6,759,046 B1 | 7/2004 | Gaudernack et al. | |

(Continued)

FOREIGN PATENT DOCUMENTS

| | | |
|---|---|---|
| JP | 2004147649 A | 5/2004 |
| WO | WO-85/04103 A1 | 9/1985 |

(Continued)

OTHER PUBLICATIONS

Tisch et al (PNAS 91: 437-438, 1994).*
Schrieber et al (Seminar. Immunol. 22: 105-112, 2010).*
Klebanoff et al (Immunol. Rev. 2011, 239: 27-44).*
Rammensee et al (MHC Ligands and Peptide Motifs, 1997, Springer, New York & Austin, Texas, USA, p. 317).*
Vaccine Protocol (Humana Press, 2003, Totowa, NJ, Ed. Andrew Robinson, Michael J. Hudson and Martin P. Cranage, pp. 121-123).*

(Continued)

*Primary Examiner* — G. R. Ewoldt
*Assistant Examiner* — Marianne DiBrino
(74) *Attorney, Agent, or Firm* — Nixon & Vanderhye, PC

(57) ABSTRACT

The present invention relates to immunogenic peptides comprising a T-cell epitope. Said peptides are modified such that CD4+ T-cell responses are obtainable that are much stronger than the CD4+ T-cell responses obtained with the same peptides not comprising said modification. In particular, the modification is the addition of a cysteine, insertion of a cysteine or mutation into a cysteine of a residue at a position adjacent to but outside the MHC-binding site of the peptide. Further disclosed are the use of such modified peptides in treating, suppressing or preventing diseases such as infectious or allergic diseases and autoimmune diseases, in preventing or suppressing graft rejection, or in the eradication of tumor cells.

Figure 1:
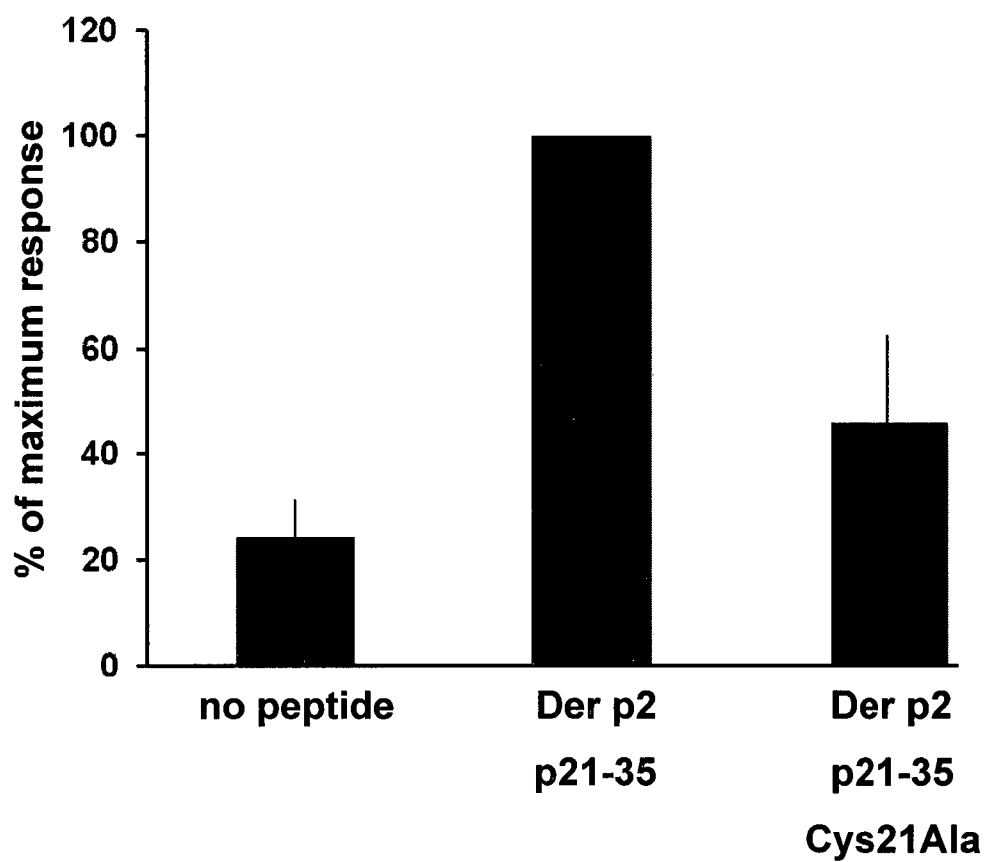

3 Claims, 3 Drawing Sheets
Specification includes a Sequence Listing.

(56) References Cited

U.S. PATENT DOCUMENTS

| | | | |
|---|---|---|---|
| 7,157,089 | B1 | 1/2007 | Mizzen et al. |
| 7,306,804 | B2 | 12/2007 | Sastry et al. |
| 7,780,882 | B2 * | 8/2010 | Chang ............... A61K 9/1272 |
| | | | 264/4.1 |
| 8,999,346 | B2 | 4/2015 | Saint-Remy |
| 9,044,507 | B2 | 6/2015 | Saint-Remy |
| 9,248,171 | B2 | 2/2016 | Saint-Remy |
| 9,249,202 | B2 | 2/2016 | Saint-Remy |
| 9,394,517 | B2 | 7/2016 | Saint-Remy |
| 9,861,661 | B2 * | 1/2018 | Saint-Remy ........... A61K 35/17 |
| 10,023,847 | B2 | 7/2018 | Saint-Remy |
| 10,617,748 | B2 * | 4/2020 | Saint-Remy ......... C12N 9/0051 |
| 10,662,232 | B2 * | 5/2020 | Saint-Remy ..... C07K 14/43531 |
| 2003/0049723 | A1 | 3/2003 | Zhang et al. |
| 2003/0104570 | A1 | 6/2003 | Cabezon Silva et al. |
| 2003/0129205 | A1 | 7/2003 | Saint-Remy et al. |
| 2003/0152581 | A1 | 8/2003 | Saint-Remy et al. |
| 2004/0077045 | A1 | 4/2004 | Zhang et al. |
| 2005/0032039 | A1 | 2/2005 | Sastry et al. |
| 2005/0107256 | A1 | 5/2005 | Barnwell et al. |
| 2005/0196386 | A1 | 9/2005 | Blazar et al. |
| 2005/0202044 | A1 | 9/2005 | Mizzen et al. |
| 2006/0182763 | A1 | 8/2006 | Kim et al. |
| 2006/0211091 | A1 | 9/2006 | Zhang et al. |
| 2006/0216301 | A1 | 9/2006 | Tahara et al. |
| 2006/0269561 | A1 | 11/2006 | Paterson et al. |
| 2007/0160620 | A1 | 7/2007 | Mizzen et al. |
| 2007/0184023 | A1 | 8/2007 | Rasmussen et al. |
| 2008/0176247 | A1 | 7/2008 | Chou et al. |
| 2009/0012004 | A1 * | 1/2009 | Sette ...................... A61K 38/08 |
| | | | 514/1.1 |
| 2010/0068193 | A1 | 3/2010 | Brunsvig et al. |
| 2010/0183652 | A1 | 7/2010 | Page et al. |
| 2010/0203083 | A1 | 8/2010 | Lux et al. |
| 2010/0303866 | A1 | 12/2010 | Saint-Remy |
| 2010/0330088 | A1 | 12/2010 | Saint-Remy |
| 2011/0002903 | A1 | 1/2011 | Saint-Remy |
| 2011/0110964 | A1 | 5/2011 | Saint-Remy |
| 2011/0111395 | A1 | 5/2011 | Saint-Remy |
| 2011/0111502 | A1 | 5/2011 | Saint-Remy |
| 2012/0009678 | A1 | 1/2012 | Saint-Remy |
| 2013/0095133 | A1 | 4/2013 | Klatzmann et al. |
| 2014/0370044 | A1 | 12/2014 | Saint-Remy |
| 2014/0377299 | A1 | 12/2014 | Saint-Remy |
| 2015/0110821 | A1 | 4/2015 | Saint-Remy |
| 2015/0216901 | A1 | 8/2015 | Saint-Remy |
| 2016/0091492 | A1 | 3/2016 | Saint-Remy et al. |
| 2016/0108103 | A1 | 4/2016 | Saint-Remy |
| 2016/0194367 | A1 | 7/2016 | Saint-Remy |
| 2016/0250255 | A1 | 9/2016 | Saint-Remy et al. |
| 2017/0100466 | A1 | 4/2017 | Saint-Remy |
| 2018/0228912 | A1 | 8/2018 | Saint-Remy et al. |
| 2018/0258154 | A1 | 9/2018 | Saint-Remy et al. |
| 2018/0346887 | A1 | 12/2018 | Saint-Remy |

FOREIGN PATENT DOCUMENTS

| | | |
|---|---|---|
| WO | WO-92/05800 A1 | 4/1992 |
| WO | WO-93/08279 A1 | 4/1993 |
| WO | WO-94/05790 A1 | 3/1994 |
| WO | 1996/026265 | 8/1996 |
| WO | WO-97/40852 A1 | 11/1997 |
| WO | WO-99/58552 A2 | 11/1999 |
| WO | WO-00/29008 A2 | 5/2000 |
| WO | WO-01/55393 A2 | 8/2001 |
| WO | WO-01/70263 A1 | 9/2001 |
| WO | WO-02/00892 A1 | 1/2002 |
| WO | WO-02/095051 A2 | 11/2002 |
| WO | WO-02/097070 A1 | 12/2002 |
| WO | WO-03/072731 A2 | 9/2003 |
| WO | WO-2004/018667 A1 | 3/2004 |
| WO | WO-2004/024766 A1 | 3/2004 |
| WO | WO-2005/012502 A2 | 2/2005 |
| WO | WO 2005-037190 A2 | 4/2005 |
| WO | WO-2005/039613 A1 | 5/2005 |
| WO | WO-2005/042575 A2 | 5/2005 |
| WO | WO-2005/086781 A2 | 9/2005 |
| WO | WO-2006/009920 A2 | 1/2006 |
| WO | WO-2006/059529 A1 | 6/2006 |
| WO | WO-2007/027954 A2 | 3/2007 |
| WO | WO-2007/104715 A2 | 9/2007 |
| WO | WO-2007/135684 A2 | 11/2007 |
| WO | WO-2008/017517 A1 | 2/2008 |
| WO | WO-2009/042215 A2 | 4/2009 |
| WO | WO-2009/100505 A1 | 8/2009 |
| WO | WO-2009/101204 A2 | 8/2009 |
| WO | WO-2009/101205 A2 | 8/2009 |
| WO | WO-2009/101206 A2 | 8/2009 |
| WO | WO-2009/101207 A1 | 8/2009 |
| WO | WO-2009/101208 A2 | 8/2009 |
| WO | WO-2009/106073 A2 | 9/2009 |
| WO | WO-2010/037395 A2 | 4/2010 |
| WO | WO2010115046 A1 * | 10/2010 |
| WO | WO-2013/113076 A1 | 8/2013 |
| WO | WO-2014/191432 A1 | 12/2014 |
| WO | WO-2015/063176 A1 | 5/2015 |
| WO | WO-2016/059236 A1 | 4/2016 |

OTHER PUBLICATIONS

Nielsen et al (PLOS Comp. Biol., 2008 4(7): 1-10) (Year: 2008).*
Heurtault et al (Pharmaceutical Res., 2009, 26(2): 276-285) (Year: 2009).*
Lamb et al (Nature, 1982, 300: 66-69) (Year: 1982).*
HLA Nomenclature (2015) (Year: 2015).*
Speicher et al (Current Protocols in Protein Science, 2002: 22.1.-22.1.19) (Year: 2002).*
Karin et al (J. Exp. Med., 1994, 180: 2227-2237) (Year: 1994).*
Celis et al (Molec. Immunol. 1994, 31(18): 1423-14360) (Year: 1994).*
Ochoa-Garay et al (Molec. Immunol., 1997, 34: 273-281) (Year: 1997).*
Fournier and Schirrmacher (Expert. Rev. Vaccines 8(1); 51-66, 2009) (Year: 2009).*
Schrieber et al (Seminar. Immunol. 22: 105-112, 2010) (Year: 2010).*
Klebanoff et al (Immunol. Rev. 2011, 239: 27-44) (Year: 2011).*
Hulo et al (Nucleic Acids, Research. 2006, 34, database issue D227-D230) (Year: 2006).*
ScanProsite user manual (2020, pp. 1-8) (Year: 2020).*
Carlier et al., "Increased synapse formation obtained by T cell epitopes containing a CxxC motif in flanking residues convert CD4+ T cells into cytolytic effectors," PLOS One 7(10):1-16 e45366 (2012).
Caro-Aguilar et al., "Chimeric epitopes delivered by polymeric synthetic linear peptides induce protective immunity to malaria," Microbes Infect. 7:1324-1337 (2005).
De La Cruz et al., "The immunologic significance of variation within malaria circumsporozoite protein sequences," J. Immunol. 142:3568-3575 (1989).
Fomenko et al., "Identity and functions of CxxC-derived motifs," Biochemistry 42:11214-11225 (2003).
International Search Report for International Application No. PCT/BE2013/000006, dated Jul. 1, 2013 (8 pages).
International Preliminary Report on Patentability for International Application No. PCT/BE2013/000006, completed May 22, 2014 (17 pages).
Written Opinion of the International Searching Authority for International Application No. PCT/BE2013/000006, dated Jul. 1, 2013 (10 pages).
Response to the International Search Report and Written Opinion of the International Searching Authority for International Application No. PCT/BE2013/000006, dated Nov. 27, 2013 (22 pages).
Written Opinion of the International Preliminary Examining Authority for International Application No. PCT/BE2013/000006, dated Feb. 14, 2014 (15 pages).
Response to the second Written Opinion for International Application No. PCT/BE2013/000006, dated Mar. 18, 2014 (17 pages).

(56) References Cited

OTHER PUBLICATIONS

Search Report for British Application No. GB1201511.1, dated May 29, 2012 (5 pages).
Frankel et al., "Characterization of diphtheria fusion proteins targeted to the human interleukin-3 receptor," Protein Eng. 13(8):575-81 (2000).
Markovic-Plese et al., "T cell recognition of immunodominant and cryptic proteolipid protein epitopes in humans," J Immunol. 155(2):982-92 (1995) (12 pages).
Examination Report No. 2 for Australian Patent Application No. 2013214700, dated Mar. 2, 2017 (3 pages).
Office Action for Russian Patent Application No. 2014135406/10(057410), dated Dec. 8, 2016 (English language translation provided) (10 pages).
*Vaccine Protocols.* Humana Press, 2nd edition. Edited by Andrew Robinson, Michael J. Hudson, and Martin P. Cranage, 120-123 (2003).
Abrahimians et al., "MHC class II-restricted epitopes containing an oxidoreductase activity prompt CD4+ T cells with apoptosis-inducing properties," Front Immunol. 6:449 (2015) (5 pages).
Aleksza et al., "Altered cytokine expression of peripheral blood lymphocytes in polymyositis and dermatomyositis," Ann. Rheum. Dis. 64:1485-1489 (2005).
Aley & Gillin, "Giardia lambiia: post-translational processing and status of exposed cysteine residues in TSA 417, a variable surface antigen" (1993) Exp Parasitol. 77, 295-305.
Apostolou et al., "Evidence for two subgroups of CD4-CD8- NKT cells with distinct TCR alpha beta repertoires and differential distribution in lymphoid tissues," J Immunol. 165(5):2481-90 (2000).
Appella et al., "Analysis of the structure of naturally processed peptides bound by class I and class II major histocompatibility complex molecules," EXS. 73:105-19 (1995).
Arunchalam et al., "Enzymatic reduction of disulfide bonds in lysosomes: Characterization of a Gamma-interferon-inducible lysosomal thiol reductase (GILT)," Proc. Natl. Acad. Sci USA 97(2):745-50 (2000).
Ascherio, "Environmental factors in multiple sclerosis," Expert Rev Neurother. 13(12 Suppl):3-9 (2013).
Azoury-Ziadeh et al., "T-Helper Epitopes Identified Within the E6 Transforming Protein of Cervical Cancer-Associated Human Papillomavirus Type 16," Viral Immunology, 1999, 12(4): 297-312.
Balato et al., "Natural killer T cells: An unconventional T-cell subset with diverse effector and regulatory functions," J Invest Dermatol. 129(7):1628-42 (2009).
Batten et al., "Immune response to stem cells and strategies to induce tolerance," Philos Trans R Soc Lond B Biol Sci. 362(1484):1343-56 (2007).
Boisgerault et al., "Differential roles of direct and indirect allorecognition pathways in the rejection of skin and corneal transplants," Transplantation 87(1):16-23 (2009).
Bolivar et al., "Molecular cloning of a zinc finger autoantigen transiently associated with interphase nucleolus and mitotic centromeres and midbodies. Orthologous proteins with nine CXXC motifs highly conserved form nematodes to humans," J Biol Chem. 274(51):36456-64 (1999). (10 pages).
Bower et al., "Two Members of the Thioredoxin-h Family Interact with the Kinase Domain of a *Brassica* S Locus Receptor Kinase," Plant Cell. 8(9):1641-50 (1996).
Braun et al., "Acute rejection in the absence of cognate recognition of allograft by T cells," J Immunol. 166(8):4879-83 (2001). (6 pages).
Brinks et al., "Immunogenicity of Therapeutic Proteins: The Use of Animal Models," Pharm Res. 28:2379-2385 (2011).
Brinster et al., "Bone Marrow-Derived Dendritic Cells Reverse the Anergic State of CD4+CD25+ T Cells without Reversing Their Suppressive Function," J Immunol. 175(11):7332-40 (2005). (10 pages).
Brinster et al., "Costimulatory effects of IL-1 on the expansion/differentiation of CD4+CD25+Foxp3+and CD4+CD25+Foxp3—T cells," J Leukoc Biol. 84(2):480-7 (2008).

Cao et al., "Prevention of gene transfer-induced inhibitor formation by nasal administration of human F.IX T cell epitope in a murine model of hemophilia B," Blood, vol. 104(11), (2004), pp. 121A-122A.
Capon et al., "The CD4-gp120 Interaction and Aids Pathogenesis," Annu Rev Immunol. 9:649-78 (1991).
Carlier et al., "Control of asthma by in vitro-induced allergen-specific regulatory T cells in the mouse," Munksgaard Allergy. 62(Suppl 83):555 (Abstract 1616) (2007).
Castano et al., "Peptide binding and presentation by mouse CD1," Science 269(5221): 223-226 (1995).
Cavone et al., "Long-term suppression of EAE relapses by pharmacological impairment of epitope spreading," Br J Pharmacol. 171(6):1501-9 (2014).
Celis et al., "Induction of anti-tumor cytotoxic T lymphocytes in normal humans using primary cultures and synthetic peptide epitopes," Proc Natl Acad Sci USA. 91(6):2105-9 (1994).
Chen et al., "Induction of dominant transplantation tolerance by an altered peptide ligand of the male antigen Dby," J Clin Invest. 113(12), 1754-1762 (2004).
Chen et al., "Glucocorticoid amplifies Il-2-dependent expansion of functional FoxP3+CD4+CD25+ T regulatory cells in vivo and enhances their capacity to suppress EAE," Eur J Immunol. 36(8):2139-49 (2006).
Chuanlin ed., Molecular Immunology, Fudan University Press, Shanghai Medical College Press; publication date: May 2001; pp. 428-429, 433-436 (English language translation provided) (15 pages).
Corthay et al., "CD4+ T Cells Cooperate with Macrophages for Specific Elimination of MHC Class II-Negative Cancer Cells," Adv Exp Med Biol. 590:195-208 (2007).
Cotton et al., "Oxidative inhibition of human soluble catechol-O-methyltransferase," J Biol Chem. 279(22):23710-8 (2004). (10 pages).
Credo Reference (2012) (cited by Examiner in Final Rejection dated Jul. 10, 2013 in U.S. Appl. No. 12/735,740). Best available copy.
Crellin et al., "Altered activation of AKT is required for the suppressive function of human CD4+CD25+ T regulatory cells," Blood 109(5):2014-2022 (2007).
Crompton et al., "Advances and challenges in malaria vaccine development," The Journal of Clinic Investigation, 2010, vol. 120, pp. 4168-4178.
Davids et al., A new family of giardial cysteine-rich non-VSP protein genes and a novel cyst protein, PLOS. One. vol. 1, (2006), e44.
Davis et al., "Interrogating the repertoire: broadening the scope of peptide-MHC multimer analysis," Nature Rev. Immunology, (2011), 11, 551-558.
Desmetz et al., "Proteomics-Based Identification of HSP60 as a Tumor-Associated Antigen in Early Stage Breast Cancer and Ductal Carcinoma in situ," Journal of Proteome Research (2008), 7, 3830-3837.
Dobrzanski, "Expanding roles for CD4T cells and their subpopulations in tumor immunity and therapy," Frontiers in Oncology, Mar. 2013, vol. 3, Article 63, pp. 1-19.
Dobrzynski et al., "Prevention of cytotoxic T lymphocyte responses to factor IX-expressing hepatocytes by gene transfer-induced regulatory T cells," Proc. Natl. Acad. Sci. U.S.A., vol. 103, (2006), pp. 4592-4597.
Eberl et al., "Tissue-specific segregation of CD1d-dependent and CD1d-independent NK T cells," J. Immunol., vol. 162, (1999), pp. 6410-6419.
Facktor et al., "Hypersensitivity to tetanus toxoid," J Allergy Clin Immunol. Jul. 1973;52(1): 1-12.
Fan et al., "Co-immunization of BALB/c mice with recombinant immunogens containing G protein fragment and chimeric CTL epitope of respiratory syncytial virus induces enhanced cellular immunity and high level of antibody response," (2005) Vaccine 23, 4453-4461.
Francois et al., "The CD4+ T-Cell Response of Melanoma Patients to a MAGE-A3 Peptide Vaccine Involves Potential Regulatory T Cells," Cancer Res. 69(10):4335-4345 (2009).

(56) References Cited

OTHER PUBLICATIONS

Lodish, et al. eds., (Molecular Cell Biology, 4th Edition, W.H. Freeman, New York, 2000, section 6.3, "Viruses: Structure, Function, and Uses").
Ge et al., "An hsp 70 fusion protein vaccine potentiates the immune response against Japanese encephalitis virus," (2007) Arch. Viral 152, 125-135.
Geluk et al., "HLA-DR binding analysis of peptides from islet antigens in IDDM," Diabetes, vol. 47, (1998), pp. 1594-1601.
GenBank: AA59610.1, 1995, p. 1.
GenBank AAA58655.1, 1994, p. 1.
GenBank FPAA051928, 1997, p. 1.
GenBank Accession No. M77349.1, worldwideweb at ncbi.nlm.nih.gov/nuccore/M77349> retrieved on Feb. 21, 2019 (3 pages).
GenPept PDB: 5GSB_A, 2017, 2 pages.
Gentile et al., "Thyroglobulin as an autoantigen: what can we learn about immunopathogenicity from the correlation of antigenic properties with protein structure?," (2004) Immunol 112 13-25.
Girardi et al., "Structure of an alpha-helical peptide and lipopeptide bound to the nonclassical major histocompatibility complex (MHC) class I molecule CD1d," J Biol Chem. 291 (20):10677-83 (2016).
Gross et al., "Simple conditioning with monospecific CD4+CD25+ regulatory T cells for bone marrow engraftment and tolerance to multiple gene products," Blood, vol. 108, No. 6, (2006), pp. 1841-1848.
Grossman et al., "Differential expression of granzymes A and B in human cytotoxic lymphocyte subsets and T regulatory cells," Blood, vol. 104, (2004), pp. 2840-2848.
Haque, "Cysteinylation of MHC Class II Ligands: Peptide Endocytosis and Reduction Within APC Influences T Cell Recognition," (2001) J. Immunol. 166, 4543-4551.
Harris et al., "Prediction of murine MHC class I epitopes in a major house dust mite allergen and induction of T1-type CD8+ T cell responses," (1997) Int. Immunol., vol. 9, No. 2, 273-280.
Haveman et al., "Induction and capture of CD4+ cytotoxic adenoviral specific T-cells in response to pan-DR binding adenoviral epitopes toward immunotherapy," Blood, vol. 106, (2005), Abstract 3238. (2 pages).
Haveman et al., "Novel pan-DR-binding T cell epitopes of adenovirus induce pro-inflammatory cytokines and chemokines in healthy donors," Int Immunol. 18(11):1521-1529 (2006).
Heemskerk et al., "Adenovirus-Specific CD4+ T Cell Clones Recognizing Endogenous Antigen Inhibit Viral Replication In Vitro through Cognate Interaction," The Journal of Immunology (2006); 177:8851-8859. (10 pages).
Ho et al., "CD4(−)CD8alphaalpha subset of CD1d-restricted NKT cells controls T cell expansion," J Immunol. 172(12):7350-8 (2004).
Hohn et al., "CD4+ tumor-infiltrating lymphocytes in cervical cancer recognize HLA-DR- restricted peptides provided by human papillomavirus-E7," J. Immunol., vol. 163, (1999), pp. 5715-5722.
Hori et al., "Control of regulatory T cell development by the transcription factor Foxp3," Science, vol. 299, (2003), pp. 1057-1061.
Hsu et al., "Assessing computational amino acid beta-turn propensities with a phage-displayed combinatorial library and directed evolution," Structure, (2006), vol. 14, pp. 1499-1510.
Iqbalsyah et al., "The CXXC motif at the N terminus of an alpha-helical peptide," (2006) Protein Sci. 15, 1945-1950.
Ise et al., "Naive CD4+ T cells exhibit distinct expression patterns in cytokines and cell surface molecules on their primary responses to varying doses of antigen," J. Immunol., vol. 168, (2002), pp. 3242-3250.
James et al., "HY peptides modulate transplantation responses to skin allografts," Int Immunol. 14(11):1333-1342 (2002).
Janeway et al., Immunobiology, 3rd edition, Garland Press Inc., 1997, p. G: 11. (3 pages).
Janssens et al., "CD4+ CD25+ T Cells Lyse Antigen-Presenting B Cells by Fas-Fas Ligand Interaction in an Epitope-Specific Manner," (2003) J. Immunol. 171, 4604-4612.
Jensen, "Acidification and Disulfide Reduction Can be Sufficient to Allow Intact Proteins to Bind MHC," (1993) J. Immunol. 150, No. 8, 3347-3356.
Joffre et al., "Induction of antigen-specific tolerance to bone marrow allografts with CD4+CD25+ T lymphocytes," Blood, vol. 103, No. 11, (2004), pp. 4216-4221.
Karin et al., "Reversal of Experimental Autoimmune Encephalomyelitis by a Soluble Peptide Variant of a Myelin Basic Protein Epitope: T Cell Receptor Antagonism and Reduction of Interferon gamma and Tumor Necrosis Factor a Production," J Exp Med. Dec. 1, 1994;180(6):2227-37.
Kasprowicz et al., "Tracking of Peptide-Specific CD4+ T-Cell Responses After an Acute Resolving Viral Infection: a Study of Parvovirus B19," Journal of Virology, Nov. 2006, vol. 80, No. 22, pp. 11209-11217.
Khare et al., "HLA class II transgenic mice authenticate restriction of myelin oligodendrocyte glycoprotein-specific immune response implicated in multiple sclerosis pathogenesis," (2003) Int. Immunol. 15, No. 4, 535-546.
Kumar et al., "Twins and endocrinology," Indian J Endocrinol Metab. Nov. 2014;18(Suppl 1):S48-52. doi: 10.4103/2230-8210.145074.
Lewin et al., "Effects of substitutions in the CXXC active-site motif of the extra-cytoplasmic thioredoxin ResA," Biochem. J. (2008), 414, 81-91.
Li et al., "Twisting immune responses for allogeneic stem cell therapy," (2009) World J Stem Cells 1(1), 30-35.
Li Pira et al., "High throughput T epitope mapping and vaccine development," The Journal of Biomedicine and Technology, (2010), vol. 2010, 12 pages.
Lindqvist et al., "Both CD4+ FoxP3+ and CD4+ FoxP3− T cells from patients with B-cell malignancy express cytolytic markers and kill autologous leukaemic B cells in vitro," Immunology 133:296-306 (2011).
Louis et al., "Contrasting CD25hiCD4+ T cells/FOXP3 patterns in chronic rejection and operational drug-free tolerance," Transplantation, vol. 81, (2006), pp. 398-407.
Mach et al., "Regulation of MHC Class II Genes: Lessons from a Disease," (1996) Ann. Rev. Immunol. 14, 301-331.
Maeda et al., "CD1d-independent NKT cells in beta 2-microglobulin-deficient mice have hybrid phenotype and function of NK and T cells," J. Immunol., vol. 172, (2004), pp. 6115-6122.
Maekawa et al., "Evidence for a Domain-Swapped CD4 Dimer as the Coreceptor for Binding to Class II MHC," (2006) J. Immunol. 176(11), 6873-6878.
Marti et al., "Conformationally Correct Expression of Membrane-Anchored *Toxoplasma gondii* SAG1 in the Primitive Protozoan *Giardia duodenalis*," Infection and Immunity, vol. 70, No. 2, Feb. 2002, p. 1014-1016.
Massilamany et al., "Detection of autoreactive CD4 T cells using major histocompatibility complex class II dextramers," BMC Immunology, (2011), 12:40 (14 pages).
Matsuda et al., "CD1d-restricted iNKT cells, the 'Swiss-Army Knife' of the immune system," Current Opinion in Immunology, vol. 20, No. 3, Jun. 1, 2008, pp. 358-368.
Matthias et al, "Disulfide exchange in domain 2 of CD4 is required for entry of HIV-1," (2002) Nature Immunol 3, No. 8, 727-732. (7 pages).
Maynard et al., "Regulatory T cells expressing interleukin 10 develop from Foxp3+ and Foxp3− precursor cells in the absence of interleukin 10," Nat. Immunol., vol. 8, (2007), pp. 931-941.
MedlinePlus Medical Dictionary (Merriam-Webster, Inc., 2017).
Merkler et al., "Myelin oligodendrocyte glycoprotein-induced experimental autoimmune encephalomyelitis in the common marmoset reflects the immunopathology of pattern II multiple sclerosis lesions," Multiple Sclerosis 12:369-374 (2006).
Moldovan et al., "CD4 Dimers Constitute the Functional Component Required for T Cell Activation," The Journal of Immunology (2002), 169:6261-6268.
Nepom, "MHC class II tetramers," The Journal of Immunology, (2012), 188, 2477-2482.
Ochoa-Garay et al., "The Ability of Peptides to Induce Cytotoxic T Cells In Vivo Does Not Strongly Correlate With Their Affinity for

(56) References Cited

OTHER PUBLICATIONS the H-2Ld Molecule: Implications for Vaccine Design and Immunotherapy," Mol Immunol (1997) 34(3):273-81.
Okubo et al., "Analysis of HLA-DRB1 0901-binding HPV-16 E7 helper T cell epitope," (2004) J Obstet Gynaecol Res. 30(2), 120-129.
Oliviera et al., "Insights into the Specificity of Thioredoxin Reductase—Thioredoxin Interactions. A Structural and Functional Investigation of the Yeast Thioredoxin System," (2010) Biochemistry 49, 3317-3326.
Papanastasiou et al., "Primary structure and biochemical properties of a variant-specific surface protein of *Giardia*," Molecular and Biochemical Parasitology. 86 (1997) 13-27.
Park et al., "Redox Regulation Facilitates Optimal Peptide Selection by MHC Class I during Antigen Processing," Cell, (2006), 127:369-382.
Peterson, "Regulatory T-cells, diverse phenotypes integral to immune homeostasis and suppression," Toxic Path. 40(2):186-204 (2012).
Printout from NetMHCIIpan Server—prediction results, dated Sep. 26, 2018, 1 page.
Qin et al., "Fusion protein of CDR mimetic peptide with Fc inhibit TNF-alpha induced cytotoxicity," Mol. Immunol., vol. 43, (2006), pp. 660-666.
Quintana et al., "Epitope spreading as an early pathogenic event in pediatric rnultiple sclerosis," Neurology 83(24):2219-26 (2014).
Racaniello, "How many viruses on earth?" Virology Blog (2013), .virology.ws/2013/09/06/how-many-viruses-on-earth/> (3 pages).
Reznik et al., "Indirect Allorecognition of Mismatched Donor HLA Class II Peptides in Lung Transplant Recipients with Bronchiolitis Obliterans Syndrome," 2001, Am. J. Transpl. vol. 1: 228-235.
Roep et al., "The problems and promises of research into human immunology and autoimmune disease," (2012) Nature Med 18(1) 48-53.
Roopenian et al., "The immunogenomics of minor histocompatibility antigens," Immunol. Rev., vol. 190, (2002), pp. 86-94.
Roper et al., "SARS vaccines: where are we?", 2009, Expert Review of Vaccines, vol. 8, pp. 887-898.
Saez-Borderias et al, "Expression and function of NKG2D in CD4+ T cells specific for human cytomegalovirus," Eur. J. Immunol., vol. 36, (2006), pp. 3198-3206.
Santin et al., "Human Papillomavirus Type 16 and 18 E7-Pulsed Dendritic Cell Vaccination of Stage IB or IIA Cervical Cancer Patients: a Phase I Escalating-Dose Trial," (2008) J. Virol. 82, No. 4, 1968-1979.
Savoldo et al., "Generation of EBV-Specific CD4+ Cytotoxic T Cells from Virus Naive Individuals," (2002) J Immunol. 168(2), 909-918.
Schultz et al., "A MAGE-A3 Peptide Presented by HLA-DP4 Is Recognized on Tumor Cells by CD4+ Cytolytic T Lymphocytes," Cancer Research 60, 6272-6275, Nov. 16, 2000.
Sette et al., "HLA supertypes and supermotifs: a functional perspective on HLA polymorphism," (1998) Curr Opinion Immunol. 10, 478-482.
Sette et al., "Epitope-based vaccines: an update on epitope identification, vaccine design and delivery," 2003, Current Opinion in Immunology, vol. 15, pp. 461-470.
Shi et al., "A novel plasma membrane-bound thioredoxin from soybean," (1996) Plant Mol. Biol. 32, 653-662 (Abstract). (1 page).
Stenstrom et al., "Natural killer T-cell populations in C57BL/6 and NK1.1 congenic BALB.NK mice—a novel thymic subset defined by BALB.NK mice," Immunology, vol. 114, (2005), pp. 336-345.
Straub et al., "Allelic variation in GAD1 (GAD67) is associated with schizophrenia and influences cortical function and gene expression," Molecular Psychiatry (2007) 12, 854-869.
Sundar et al., "Generation of Epstein-Bar virus antigen-specific suppressor T cells in vitro," Int. J. Cancer, vol. 35, (1985), pp. 351-357.
Taylor et al., "T regulatory cells and allergy," Microbes and Infection, vol. 7, (2005), pp. 1049-1055.

Texier et al., "On the diversity and heterogeneity of H-2d-restricted determinants and T cell epitopes from the major bee venom allergen," (1999) Int Immunol. 11(8), 1313-1325.
Thomson et al., "Targeting a Polyepitope Protein Incorporating Multiple Class II-Restricted Viral Epitopes to the Secretory/Endocytic Pathway Facilitates Immune Recognition by CD4+ Cytotoxic T Lymphocytes: a Novel Approach to Vaccine Design," J. of Virol, 1998, 72(3):2246-2252.
Tindle et al., "A "public" T-helper epitope of the E7 transforming protein of human papillomavirus 16 provides cognate help for several E7 B-cell epitopes from cervical cancer-associated human papillomavirus genotypes," (1991) Proc Natl. Acad. Sci 88, 5887-5891.
Toyokawa et al., "Relative Contribution of Direct and Indirect Allorecognition in Developing Tolerance After Liver Transplantation," 2008 Liver Transpl. 14(3) 346-357. (23 pages).
Tsuji et al., "Antigen-specific, CD4+CD25+ regulatory T cell clones induced in Peyer's patches," Int. Immunol., vol. 15, (2003),pp. 525-534.
U.S. Appl. No. 16/091,549, unpublished application.
UniProt P01906.2, 2017 (6 pages).
UniProt O15523.2, 2017 (7 pages).
Voo et al., "Functional characterization of EBV-encoded nuclear antigen 1-specific CD4+ helper and regulatory T cells elicited by in vitro peptide stimulation," Cancer Res., vol. 65, (2005), pp. 1577-1586.
Wang et al., "Generation and characterization of HLA-A*2.1 restricted and Prostein31-39 specific NKT cell lines," Acta Academiae Medicine Militaris Tertiae. 28(16):1652-1655 (2006) (English language translation provided) (11 pages).
Wang, "Immune suppression by tumor-specific CD4+ regulatory T-cells in cancer," Semin. Cancer Biol., vol. 16, (2006), pp. 73-79.
Weissert et al., "MHC Class II-Regulated Central Nervous System Autoaggression and T Cell Responses in Peripheral Lymphoid Tissues Are Dissociated in Myelin Oligodendrocyte Glycoprotein-Induced Experimental Autoimmune Encephalomyelitis," (2001) J. Immunol. 166, 7588-7599.
Wekerle et al., "Autoimmunity's next top models," (2012) Nature Med. 18(1), 66-70.
Wiker et al., "Cloning, expression and significance of MPT53 for identification of secreted proteins of *Mycobacterium tuberculosis*," Microb. Pathog., vol. 26, (1999), pp. 207-219.
Wobus et al., "Embryonic Stem Cells: Prospects for Developmental Biology and Cell Therapy," (2005) Physiol Rev 85: 635-678.
Wood et al., "Regulatory T cells in Transplantation tolerance," Nat. Rev. Immunol., vol. 3, (2003), pp. 199-210.
Wooldridge et al., "Tricks with tetramers: how to get the most from multimeric peptide-MHC," Immunology, 2009, 126(2): 147-64.
Written Description Training Materials, Revision 1, Mar. 25, 2008, U.S. Patent and Trademark Office.
Wu et al., "Engineering an intracellular pathway for major histocompatibility complex class II presentation of antigens," (1995) Proc. Natl. Acad. Sci. 92, 11671-11675.
Zeng at al., "Crystal structure of mouse CD1: An MHC-like fold with a large hydrophobic binding groove," Science. 277: 339-345 (1997).
Zhang et al., "A MAGE-3 Peptide Presented by HLA-DR1 to CD4+ T Cells That Were Isolated from a Melanoma Patient Vaccinated with a MAGE-3 Protein," J Immunol. 171:219-225 (2003).
Zhao et al., "Activated CD4+CD25+ T cells selectively kill B Lymphocytes," Blood, vol. 107, No. 10; pp. 3925-3932; May 15, 2006.
Summons to attend oral proceedings pursuant to Rule 115(1) EPC for European Patent Application No. 13709300.1 dated Dec. 21, 2018 (20 pages).
Hemmer et al., "Minimal peptide length requirements for CD4(+) T cell clones—implications for molecular mimicry and T cell survival," Int Immunol. 12(3):375-383 (2000).
Vignali et al., "Amino acid residues that flank core peptide epitopes and the extracellular domains of CD4 modulate differential signaling through the T cell receptor," J Exp Med. 179(6):1945-56 (1994).

(56) References Cited

OTHER PUBLICATIONS

Lovitch et al., "Amino-terminal flanking residues determine the conformation of a peptide-class II MHC complex," J Immunol. 176(5):2958-68 (2006).
Abrahimians et al., "Thioreductase-Containing Epitopes Inhibit the Development of Type 1 Diabetes in the NOD Mouse Model," Frontiers in Immunology 7(67):1-10 (2016).
Database Geneseq "Human preproinsulin (PPI) antigenic peptide, Seq ID 164," retrieved from EBI accession No. GSP:BDK51134, Database accession No. BDK51134 [Online] Jan. 26, 2017 (Jan. 26, 2017) (2 pages).
International Search Report and Written Opinion of the International Searching Authority for International Application No. PCT/EP2018/055501, dated May 4, 2018 (13 pages).
Pillai et al., "Host NKT Cells Can Prevent Graft-versus-Host Disease and Permit Graft Antitumor Activity after Bone Marrow Transplantation," J Immunol. 178(10):6242-51 (2007).
Extended European Search Report for European Patent Application No. 17160085.1, dated Jun. 6, 2017 (7 pages).

\* cited by examiner

# MODIFIED EPITOPES FOR BOOSTING CD4+ T-CELL RESPONSES

CROSS-REFERENCE TO RELATED APPLICATIONS

This application is the U.S. national stage of PCT/BE2013/000006, filed Jan. 30, 2013, which claims the benefit of U.S. provisional application No. 61/592,404, filed Jan. 30, 2012 and United Kingdom application no. GB 1201511.1, filed Jan. 30, 2012.

FIELD OF THE INVENTION

The present invention relates to immunogenic peptides comprising a T-cell epitope. Said peptides are modified such that CD4+ T-cell responses are obtainable that are much stronger than the CD4+ T-cell responses obtained with the same peptides not comprising said modification. In particular, the modification is the addition of a cysteine, insertion of a cysteine or mutation into a cysteine of a residue at a position adjacent to but outside the MHC-binding site of the peptide. Further disclosed are the use of such modified peptides in treating, suppressing or preventing diseases such as infectious and allergic diseases and autoimmune diseases, in preventing or suppressing graft rejection, or in the eradication of tumor cells.

BACKGROUND OF THE INVENTION

The aim of vaccination against pathogens is to elicit a specific immune response that is as strong as possible. Such vaccination makes use of antigens, which have a weak intrinsic immunogenicity. The reasons for such weak immunogenicity are related to the large diversity of histocompatibility complexes in the human population. Such complexes, either class I for the presentation to CD8+ T cells or class II for presentation to CD4+ T cells, present the antigen to T cells at the surface of specialized cells, called antigen-presenting cells. The strength at which T cells are activated depends on the strength and duration of the synapse formed between an antigen-presenting cell loaded with a peptide obtained after antigen processing and specific T cells.

The conventional method by which weak immunogenicity is circumvented is the addition of an adjuvant. Several of these adjuvants have been described, from aluminum salts to oil emulsions. The mechanism by which adjuvants increase immunogenicity is non-specific and depends on the type of adjuvant used. However, in many cases, the use of adjuvants is limited because of inflammatory adverse effects.

A general method by which the immunogenicity of vaccine antigens would be increased specifically is very much desirable. This concerns vaccine antigens to extracellular pathogens such as bacteria or parasites, as well as vaccine antigens to intracellular pathogens such as viruses.

Immune responses can be suppressed by regulatory T cells. Such cells, which belong to the natural subset centrally selected in the thymus or the peripheral subsets obtained in the periphery by antigen encounter, use a number of mechanisms to suppress immune responses, including the production of suppressive cytokines such as IL-10 or TGF-beta, deprivation of target cells from essential nutrients such as arginine or tryptophan, or cell contacts. The repertoire of natural regulatory T cells is auto-reactive as the result of selection upon autoantigen presentation in the thymus. Peripheral or induced regulatory T cells are formed and activated by contact with either autoantigens or alloantigens.

The percentage of antigen-specific regulatory T cells is very low and these cells are difficult to expand in vitro. Besides, methods to expand such cells in vivo are not very successful. For example, administration of synthetic peptides encompassing MHC (major histocompatibility complex) class II epitopes in the absence of adjuvant elicits the expansion of regulatory T cells producing IL-10. Yet, the activation and expansion of regulatory T cells is known to be strictly dependent of co-stimulation, namely activation of antigen-presenting cells resulting in surface expression of costimulatory molecules, including those of the B7 family, which interact with surface CD28 at the T cell surface. Mice deficient in CD28 do not produce regulatory T cells and have a largely increased incidence of autoimmune diseases.

A general method by which the immunogenicity of vaccine antigens required to expand regulatory T cells would be improved is therefore much required. Vaccine antigens in this setting include autoantigens or alloantigens.

Many tumors express antigens that may serve as target for therapy. Such antigens are shed by the tumor and presented to the host immune system by host antigen-presenting cell. This process, called the indirect antigen presentation pathway, elicits tumor specific CD4+ and CD8+ T cells. In most cases, however, the tumor cells do not express MHC class II determinants and an efficient immune response relies only on CD8+ T cells recognizing tumor-derived peptides presented by MHC class I determinants. This is poorly efficient as illustrated by the numerous attempts to boost tumor-specific CD8+ T cells using class I restricted peptides (Boon et al. 2006, Ann Rev Immunol 24, 175-208). Novel strategies are therefore required.

There has been some suggestion that tumor specific CD4+ T cells can play a role in tumor rejection even when the tumor does not express MHC class II determinants (Perez-Diez et al. 2007, Blood 15, 5346-5354), suggesting an indirect effect on either NK cells or on stroma cells. However, no attempt to boost the CD4+ T cell response has been proposed.

A general method by which CD4+ T cells specific response for tumor antigens presented by the indirect pathway would be increased is much desirable. This concerns tumors producing oncogens or protooncogens, virus-derived proteins, surviving factors or clonotypic determinants.

The common desideratum in the above thus is the finding of an agent or method to boost CD4+ T cell activation, which in turns results in one or more of increased effector CD4+ T cell-function, increased regulatory T-cell function and increased CD8+ T cell-activation. CD4+ T cells are, when activated, not naturally cytotoxic or cytolytic. It has been disclosed that the addition of a redox-active peptide tag (a "CXXC" or "CXX[S/T]" or "[S/T]XXC" peptide motif) to a T-cell antigen not naturally containing such tag converts a CD4+ T cell activated by such modified T-cell antigen from a non-cytolytic into a cytolytic CD4+ T-cell (WO 2008/017517; WO 2009/100505; WO 2009/100204; WO 2009/100205; WO 2009/100206; WO 2009/100207; WO 2009/100208). None of these documents, however, describes enhancement of the "normal" activation of CD4+ T cells without converting non-cytolytic into cytolytic CD4+ T-cells.

SUMMARY OF THE INVENTION

An aspect of the present invention relates to isolated immunogenic peptides comprising:

a) a T cell epitope which binds to the cleft of an MHC protein, and b) a sequence of between 1 and 6 amino acids at the n-terminal and/or c-terminal side of the epitope and comprising a cysteine residue, with the proviso that the cysteine does not occur in a sequence with the motif Cxx[CST] or [CST]xxC, when this motif, if occurring, is adjacent to the epitope or separated from the epitope by at most 7 amino acids, wherein said isolated immunogenic peptide is an artificial peptide wherein the sequence defined in part a) and b) differs from the sequence as occurring in the wild type sequence of said antigenic protein.

In particular embodiments, the sequence defined in part b) contains only one cysteine.

In specific embodiments, the epitope is a MCH class II epitope.

In particular embodiments the peptide have a length of between 9 and 100 amino acids, between 9 and 50 amino acids, or between 9 and 20 amino acids.

In other particular embodiments, the cysteine amino acid is located N- or C-terminally adjacent to the epitope, without amino acids between the epitope and the cysteine amino acid.

Examples of disease associated T cell epitopes in the context of the present invention are T cell epitopes of an infectious agents, T cell epitopes of a self antigens, of allergens, of allofactors or of allograft antigens. Other examples of disease-associated T cell epitopes are T cell epitopes specific or preferential to a tumor.

The present invention relates to immunogenic peptides. In particular said immunogenic peptides are consisting of:
(i) a T cell epitope, with the proviso that if said T cell epitope is comprising amino acid residues other than and flanking the amino acid residues binding to an MHC, said flanking amino acid residues are not naturally comprising a cysteine amino acid within up to 6 amino acids adjacent to the MHC binding region of said T cell epitope and are not comprising a mono- or dicysteinic redox motif; and
(ii) a cysteine amino acid at a position outside the MHC-binding region of the T cell epitope wherein said cysteine amino acid is added to or inserted into to the T cell epitope at said position, or wherein said cysteine amino acid results from mutating a non-cysteine amino acid at said position of the T cell epitope to a cysteine.

In the immunogenic peptides according to the invention, said cysteine amino acid of (ii) may be added or inserted into the T cell epitope at a position separated by at most 5 amino acids from the MHC-binding region, or said cysteine amino acid of (ii) may result from the mutation of a non-cysteine amino acid to a cysteine amino acid at a position separated by at most 5 amino acids from the MHC-binding region.

Furthermore, in the immunogenic peptides according to the invention, said cysteine amino acid of (ii) may be separated from the T cell epitope MHC-binding region by an artificial linker amino acid sequence of at most 5 amino acids.

In any one of the immunogenic peptides according to the invention, said cysteine amino acid may be located N- or C-terminally adjacent to the MHC binding region.

In any one of the immunogenic peptides according to the invention, said disease-associated T cell epitope include a T cell epitope of an infectious agent, of a self antigen, of an allergen, of an allofactor or of an allograft antigen, or a T cell epitope specific or preferential to a tumor.

The invention further pertains to compositions comprising an immunogenic peptide according to the invention and further at least one of a solvent, diluent, carrier or adjuvant.

The immunogenic peptides according to the invention or the compositions according to the invention comprising such peptides are suitable for use as a medicament. Depending on the nature of the T cell epitope contained in the immunogenic peptide, the medicament comprising the immunogenic peptide can be used as a medicament for treating or preventing an infectious disease, as a medicament for treating, preventing or suppressing an autoimmune disease, an allergic disease, for preventing or suppressing graft rejection, for preventing or suppressing an immune reaction which is neutralizing an allofactor, or for treating, preventing or eradicating a tumor or cancer cells. In general, the immunogenic peptides according to the invention or the compositions according to the invention comprising such peptides are for use as a medicament for inducing an effective CD4+ T cell response which can lead to an effective effector CD4+ T cell response, to an effective regulatory T cell response, and/or to an effective activation of CD8+ T cells.

Herein the activation of CD8+ T cells is an indirect activation via the production of cytokines such as Interleukin 2 by superactivated CD4+ T cells.

Another aspect of the invention relates to methods for preparing a peptide of an antigenic protein capable of eliciting a CD4+ T-cell response, comprising the steps of
(a) providing a peptide sequence consisting of a T-cell epitope of said antigenic protein, and
(b) linking to the peptide sequence of (a) a sequence comprising a cysteine residue wherein the cysteine residue is separated by at most 5 amino acids from the epitope sequence, with the proviso that said cysteine does not occur as a cysteine in a sequence with motif [CST]-xx-C or C-xx-[CST], when such motif if, if occurring, is adjacent to said MHC binding region or separated from said MHC binding region by at most 7 amino acids.
(c) synthesizing a peptide comprising the sequence as defined in steps a) and b).

Herein the sequence of a T cell epitope in an antigenic protein can be determined by computer algorithms and/or biochemical assay.

In this method the peptide sequence of part b can obtained by modifying the amino acid sequence of the antigenic protein in a region up to 6 amino acids N terminal or C terminal of the epitope sequence.

This can be done by a mutation is selected from the group consisting of the introduction of a cysteine, the deletion of a cysteine which occurs as a cysteine in a motif [CST]-xx-C or C-xx-[CST], and the deletion of a cysteine at one position and the introduction of a cysteine at another position.

Alternatively the peptide sequence of part b can an artificial sequence unrelated to the sequence of the antigenic protein in a region up to 6 amino acids N terminal or C terminal of the epitope sequence.

The use of the immunogenic peptides according to the invention or of the compositions comprising such peptides for the production of a medicament for treating, preventing or suppressing an autoimmune disease, an allergic disease, for preventing or suppressing graft rejection, for preventing or suppressing an immune reaction which is neutralizing an allofactor, or for treating, preventing or eradicating a tumor or cancer cells is also contemplated.

LEGENDS TO FIGURES

FIG. 1. Proliferation of a Der p2 p21-35 peptide-specific CD 4+T cell clone in the presence of naïve antigen-presenting cell not loaded with any peptide ("no peptide") or loaded with the natural p21-35 peptide ("Der p2 p21-35"), or loaded with the p21-35 peptide wherein the cysteine at position 21 (N-terminal amino acid of p21-35 peptide) was mutated to alanine ("Der p2 p21-35 Cys21Ala").

Figure 2:
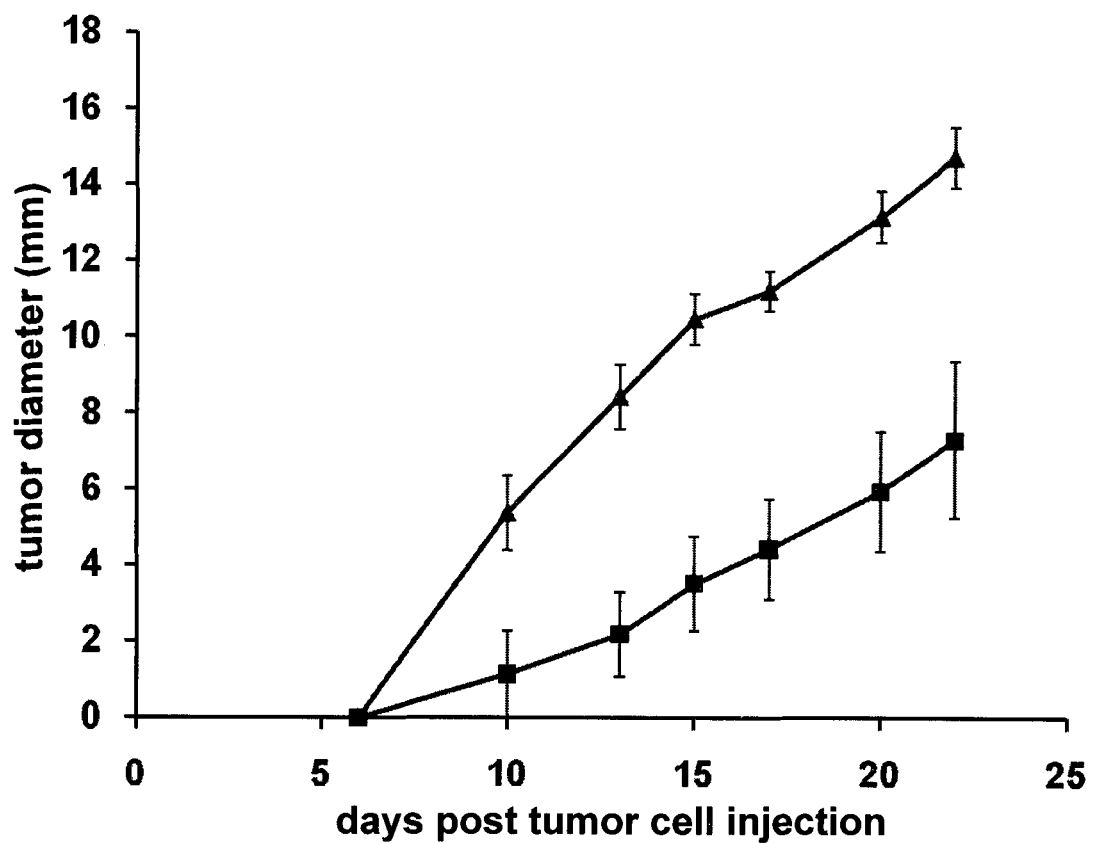

FIG. 2. Growth of NPM-ALK tumor in immunocompetent C57BL/6 mice not pre-treated (triangles) or pre-treated by preimmunisation with a T cell antigen derived from the ALK protein, with said T cell antigen comprising a cysteine adjacent to the MHC-binding region of the T cell antigen (squares).

Figure 3:
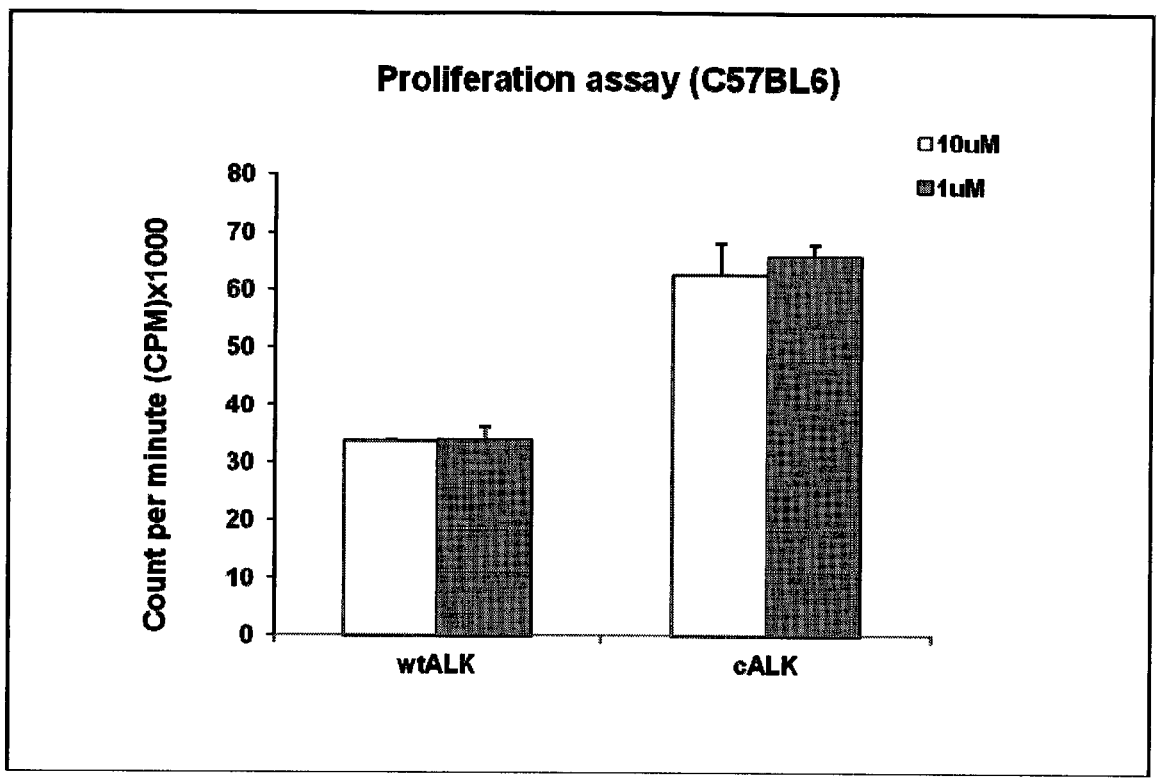

FIG. 3. Proliferation rate of CD4+ T cells, as assessed by incorporation of tritiated thymidine, after stimulation of cells with (a) a peptide of sequence GAA EGG WTGP-GAGPR (SEQ ID NO:14), corresponding to aminoacids 1541-1555 of the ALK protein in its natural or wildtype (wtALK in the figure) sequence or with (b) a peptide of sequence CGG WTGPGAGPR (SEQ ID NO:15), in which a single cysteine was added at position 1544 of the ALK protein.

DETAILED DESCRIPTION OF THE INVENTION

Definitions

The term "peptide" when used herein refers to a molecule comprising an amino acid sequence of between 2 and 200 amino acids, connected by peptide bonds, but which can in a particular embodiment comprise non-amino acid structures (like for example a linking organic compound). Peptides according to the invention can contain any of the conventional 20 amino acids or modified versions thereof, or can contain non-naturally occurring amino acids incorporated by chemical peptide synthesis or by chemical or enzymatic modification.

The term "epitope" when used herein refers to one or several portions (which may define a conformational epitope) of a protein or factor which is/are specifically recognized and bound by an antibody or a portion thereof (Fab', Fab2', etc.) or a receptor presented at the cell surface of a B or T cell lymphocyte, and which is able, by said binding, to induce an immune response.

The term "antigen" when used herein refers to a structure of a macromolecule comprising one or more hapten(s) (eliciting an immune response only when attached to a carrier) and/or comprising one or more T cell epitopes. Typically, said macromolecule is a protein or peptide (with or without polysaccharides) or made of proteic composition and comprises one or more epitopes; said macromolecule can herein alternatively be referred to as "antigenic protein" or "antigenic peptide".

The term "allofactor" refers to a protein, peptide or factor (i.e., any molecule) displaying polymorphism when compared between 2 individuals of the same species, and, more in general, any protein, peptide or factor that induces an (alloreactive) immune response in the subject receiving the allofactor.

The term "T cell epitope" or "T-cell epitope" in the context of the present invention refers to a dominant, sub-dominant or minor T cell epitope, i.e., a part of an antigenic protein or factor that is specifically recognized and bound by a receptor at the cell surface of a T lymphocyte. Whether an epitope is dominant, sub-dominant or minor depends on the immune reaction elicited against the epitope. Dominance depends on the frequency at which such epitopes are recognized by T cells and able to activate them, among all the possible T cell epitopes of a protein. In particular, a T cell epitope is an epitope bound by MHC class I or MHC class II molecules. A T cell epitope in a protein sequence can be identified by functional assays and/or one or more in silico prediction assays. The amino acids in a T cell epitope sequence are numbered according to their position in the binding groove of the MHC proteins. A T-cell epitope present within the peptides of the invention may consist of between 8 and 25 amino acids, of between 8 and 16 amino acids, or may consist of 8, 9, 10, 11, 12, 13, 14, 15 or 16 amino acids. The T cell epitope of the immunogenic peptides of the invention can correspond either to a natural epitope sequence of a protein or can be a modified version thereof, provided the modified T cell epitope retains its ability to bind within the MHC cleft, similar to the natural T cell epitope sequence. The modified T cell epitope can have the same binding affinity for the MHC protein as the natural epitope, but can also have a lowered affinity. In particular embodiments the binding affinity of the modified peptide is no less than 10-fold less than the original peptide, more particularly no less than 5 times less.

The term "MHC" refers to "major histocompatibility antigen". In humans, the MHC genes are known as HLA ("human leukocyte antigen") genes. Although there is no consistently followed convention, some literature uses HLA to refer to HLA protein molecules, and MHC to refer to the genes encoding the HLA proteins. As such the terms "MHC" and "HLA" are equivalents when used herein. The HLA system in man has its equivalent in the mouse, i.e., the H2 system. The most intensely-studied HLA genes are the nine so-called classical MHC genes: HLA-A, HLA-B, HLA-C, HLA-DPA1, HLA-DPB1, HLA-DQA1, HLA-DQB1, HLA-DRA, and HLA-DRB1. In humans, the MHC is divided into three regions: Class I, II, and III. The A, B, and C genes belong to MHC class I, whereas the six D genes belong to class II. MHC class I molecules are made of a single polymorphic chain containing 3 domains (alpha 1, 2 and 3), which associates with beta 2 microglobulin at cell surface. Class II molecules are made of 2 polymorphic chains, each containing 2 chains (alpha 1 and 2, and beta 1 and 2).

Class I MHC molecules are expressed on virtually all nucleated cells. Peptide fragments presented in the context of class I MHC molecules are recognized by CD8+ T lymphocytes (cytotoxic T lymphocytes or CTLs). CD8+ T lymphocytes frequently mature into cytotoxic effectors which can lyse cells bearing the stimulating antigen. Class II MHC molecules are expressed primarily on activated lymphocytes and antigen-presenting cells. CD4+ T lymphocytes (helper T lymphocytes or HTLs) are activated with recognition of a unique peptide fragment presented by a class II MHC molecule, usually found on an antigen presenting cell like a macrophage or dendritic cell. CD4+ T lymphocytes proliferate and secrete cytokines that either support an antibody-mediated response through the production of IL-4 and IL-10 or support a cell-mediated response through the production of IL-2 and IFN-gamma.

Functional HLAs are characterized by a deep binding groove to which endogenous as well as foreign, potentially antigenic peptides bind. The groove is further characterized by a well-defined shape and physico-chemical properties. HLA class I binding sites are closed, in that the peptide termini are pinned down into the ends of the groove. They are also involved in a network of hydrogen bonds with conserved HLA residues. In view of these restraints, the length of bound peptides is limited to 8-10 residues. However, it has been demonstrated that peptides of up to 12 amino acid residues are also capable of binding HLA class I. Superposition of the structures of different HLA complexes confirmed a general mode of binding wherein peptides adopt a relatively linear, extended conformation.

In contrast to HLA class I binding sites, class II sites are open at both ends. This allows peptides to extend from the actual region of binding, thereby "hanging out" at both ends. Class II HLAs can therefore bind peptide ligands of variable length, ranging from 9 to more than 25 amino acid residues. Similar to HLA class I, the affinity of a class II ligand is determined by a "constant" and a "variable" component. The constant part again results from a network of hydrogen bonds formed between conserved residues in the HLA class II groove and the main-chain of a bound peptide. However, this hydrogen bond pattern is not confined to the N- and C-terminal residues of the peptide but distributed over the whole chain. The latter is important because it restricts the conformation of complexed peptides to a strictly linear mode of binding. This is common for all class II allotypes. The second component determining the binding affinity of a peptide is variable due to certain positions of polymorphism within class II binding sites. Different allotypes form different complementary pockets within the groove, thereby accounting for subtype-dependent selection of peptides, or specificity. Importantly, the constraints on the amino acid residues held within class II pockets are in general "softer" than for class I. There is much more cross reactivity of peptides among different HLA class II allotypes. The sequence of the +/−9 amino acids of an MHC class II T cell epitope that fit in the groove of the MHC II molecule are usually numbered P1 to P9. Additional amino acids N-terminal of the epitope are numbered P−1, P−2 and so on, amino acids C-terminal of the epitope are numbered P+1, P+2 and so on.

The term "tumor-associated antigen" refers to any protein, peptide or antigen associated with (carried by, produced by, secreted by, etc.) a tumor or tumor cell(s). Tumor-associated antigens may be (nearly) exclusively associated with a tumor or tumor cell(s) and not with healthy normal cells or may be overexpressed (e.g., 10 times, 100 times, 1000 times or more) in a tumor or tumor cell(s) compared to healthy normal cells. More particularly a tumor-associated antigen is an antigen capable of being presented (in processed form) by MHC determinants of the tumor cell. Hence, tumor-associated antigens are likely to be associated only with tumors or tumor cells expressing MHC molecules. Tumor associated antigens may also be referred to as antigens specific or preferential to a tumor. T cell epitopes comprised in a tumor-associated antigen are referred to also herein as T cell epitopes specific or preferential to a tumor.

An "allergen" is defined as a substance, usually a macromolecule or a proteic composition which elicits the production of IgE antibodies in predisposed, particularly genetically disposed, individuals (atopics) patients.

The term "therapeutically effective amount" refers to an amount of the peptide of the invention or derivative thereof, which produces the desired therapeutic or preventive effect in a patient. For example, in reference to a disease or disorder, it is the amount which reduces to some extent one or more symptoms of the disease or disorder, and more particularly returns to normal, either partially or completely, the physiological or biochemical parameters associated with or causative of the disease or disorder. According to one particular embodiment of the present invention, the therapeutically effective amount is the amount of the peptide of the invention or derivative thereof, which will lead to an improvement or restoration of the normal physiological situation. For instance, when used to therapeutically treat a mammal affected by an immune disorder, it is a daily amount peptide/kg body weight of the said mammal. Alternatively, where the administration is through gene-therapy, the amount of naked DNA or viral vectors is adjusted to ensure the local production of the relevant dosage of the peptide of the invention, derivative or homologue thereof.

The term "derivative" when used herein with reference to the peptides of the invention refers to molecules which contain at least the peptide active portion (i.e. capable of eliciting cytolytic CD4+ T cell activity) and, in addition thereto comprises a complementary portion which can have different purposes such as stabilizing the peptides or altering the pharmacokinetic or pharmacodynamic properties of the peptide.

The terms "peptide-encoding polynucleotide (or nucleic acid)" and "polynucleotide (or nucleic acid) encoding peptide" when used herein refer to a nucleotide sequence, which, when expressed in an appropriate environment, results in the generation of the relevant peptide sequence or a derivative or homologue thereof. Such polynucleotides or nucleic acids include the normal sequences encoding the peptide, as well as derivatives and fragments of these nucleic acids capable of expressing a peptide with the required activity. According to one embodiment, the nucleic acid encoding the peptides according to the invention or fragment thereof is a sequence encoding the peptide or fragment thereof originating from a mammal or corresponding to a mammalian, most particularly a human peptide fragment.

DESCRIPTION

As described above, the addition of a 4-amino acid redox-active peptide tag ("CXXC" or "CXX[S/T]" or "[S/T]XXC" motif) to a T cell antigen (and with said tag being outside of and flanking the MHC-binding site of the antigen) converts a CD4+ T cell into a cytolytic CD4+ T cell upon activation. This conversion is normally not occurring naturally and cytolytic cells induced during a natural immune response are restricted to cytolytic CD8+ T cells. In further work studying the above system and leading to the present invention, it was found that when the redox activity of the peptide tag added to a T cell antigen was abolished by converting at least one of the cysteine residues in the redox-active tag to a non-cysteine residue (yet excluding serine or threonine as non-cysteine residue), that then CD4+ T cells could be activated. Surprisingly, however, this activation was much stronger than in the case when no cysteine residue at all was present in the peptide tag. It was furthermore found that the presence in a T cell antigen of a single cysteine residue adjacent to the MHC-binding region or site of said T cell antigen was sufficient to elicit said stronger CD4+ T cell activation.

Without being bound to any theory or mode of action, there thus seems to be a continuum in types of activation of CD4+ T cells: (i) a "basal" natural activation by T cell antigens not comprising a redox-active peptide tag or single cysteine in the region flanking the MHC-binding site as described above, (ii) an increased activation (compared to the basal activation) by T cell antigens comprising a single cysteine in the region adjacent to/flanking the MHC-binding site, and (iii) conversion of the CD4+ T cell to a cytolytic CD4+ T cell when activated by T cell antigens comprising a redox-active peptide tag in the region adjacent to/flanking the MHC-binding site of the T cell antigen.

The present invention relates to isolated T cell antigens modified to comprise outside the MHC-binding site of the antigen peptide sequence a cysteine residue, as well as to the use of such modified antigens for increasing the activation of CD4+ T cells. Said increased activation is in comparison to the activation of CD4+ T cells by T cell antigens not comprising outside the antigen peptide sequence such cysteine residue. These immunogenic peptides according to the invention as well as their uses are described in more detail hereafter.

The present invention thus relates to immunogenic peptides. In particular said immunogenic peptides are consisting of:
(i) a T cell epitope, wherein if said T cell epitope is comprising amino acid residues flanking the amino acid residues binding to an MHC (or flanking the amino acid residues constituting the MHC binding site of the T cell epitope), said flanking amino acid residues are not naturally comprising a cysteine amino acid at a position within up to 6 amino acids adjacent to (and contiguous with) the MHC binding region of said T cell epitope and are not comprising a mono- or dicysteinic redox or redox-active motif; and
(ii) a cysteine amino acid at a position outside the MHC-binding region of the T cell epitope wherein said cysteine amino acid is added to or inserted into to the T cell epitope at said position, or wherein said cysteine amino acid results from mutating a non-cysteine amino acid at said position of the T cell epitope to a cysteine.

The immunogenic peptides of the invention can be schematically represented as A-L-B or B-L-A, wherein A represents a T-cell epitope, L represents a linker and B represents a free cysteine residue. The immunogenic peptides of the present invention can be made by chemical synthesis, which allows the incorporation of non-natural amino acids. Accordingly, the cysteine residue can be replaced by another amino acid with a thiol group such as mercaptovaline, homocysteine or other natural or non-natural amino acids with a thiol function. In order to have reducing activity, the cysteine residue should not occur as part of a cysteine disulfide bridge. Nevertheless, the cysteine residue can be modified such as through methylation, as methylated cysteine is converted into cysteine with free thiol groups in vivo.

The immunogenic peptides of the invention can vary substantially in length, e.g. from about 12-13 amino acids (a T-cell epitope of 8-9 amino acids and the 4 flanking amino acids containing the cysteine residue) to up to 50 or more amino acids. For example, an immunogenic peptide according to the invention may comprise an endosomal targeting sequence of 40 amino acids, a flanking sequence of about 6 amino acids comprising a cysteine, and a T cell epitope peptide of 9 amino acids. In particular embodiments, the immunogenic peptides of the invention consist of between 12 amino acids and 20 up to 25, 30, 50, 75, 100 or 200 amino acids. In a more particular embodiment, the peptides consist of between 10 and 20 amino acids. Such peptides can optionally be coupled to an endosomal-targeting signal.

In the above, the T cell epitope is meant to be a contiguous part of a naturally occurring protein. Such contiguous part can be the result of digestion of the naturally occurring protein that is digested by e.g. the proteasome or endosome of antigen-presenting cells. Alternatively, such part may be man-made (e.g. recombinantly or synthetically/chemically produced). In all cases, the T cell epitope has an amino acid sequence which is the same as the part of the naturally occurring protein, i.e., it has a contiguous amino acid sequence as occurring in nature/naturally.

A T cell epitope may consist solely of the amino acids binding to the groove of a major histocompatibility complex (MHC), or may comprise the same amino acids together with flanking amino acid residues. Such flanking residues are not contributing to the binding of the epitope to the MHC and are "hanging" outside the MHC groove. Flanking residues may be present at the N- and/or C-terminus of the MHC-binding part of the T cell epitope. In the immunogenic peptides of the present invention, said cysteine residue is located such that, when the epitope fits into the MHC groove, said cysteine residue remains outside of the MHC binding groove. T cell epitopes comprising flanking residues may naturally comprise in their amino acid sequence a cysteine residue, such as the T cell epitope used in Example 2 herein which is partly at the origin of the current invention (said T cell epitope is comprising 2 flanking amino acid residues at the N-terminal side of and naturally contiguous with the MHC-binding part; said flanking amino acid residues comprise a naturally occurring cysteine). T cell epitopes naturally comprising a cysteine in a position as required according to the invention are excluded from the current invention when a cysteine residue is occurring in the contiguous natural sequence within up to 6 amino acids adjacent to, i.e., immediately N- or C-terminal of and naturally contiguous with the MHC-binding amino acids. Further excluded from the current invention are immunogenic peptides comprising flanking amino acid residues outside the MHC-binding site wherein the flanking amino acid residues comprise a mono- or dicysteinic redox motif (either naturally, non-naturally, or after addition of/insertion of/mutation into a cysteine as dictated by the current invention). As explained above, the presence of the redox motif in the latter peptides convert naturally non-cytolytic CD4+ T-cells into cytolytic CD4+ T-cells, i.e. into CD4+ T-cells with characteristics not wanted in the current invention. Dicysteinic redox motifs in the above are meant to be "CXXC"-motifs, whereas monocysteinic redox motifs are meant to be "CXX[S/T]" or "[S/T]XXC" motifs. Immunogenic peptides according to the invention comprising a cysteine amino acid within their MHC-binding region (or alternatively, which are buried in the MHC-cleft upon binding to an MHC molecule) are not excluded from the invention.

In the immunogenic peptides according to the invention, said cysteine amino acid of (ii) may be added to or inserted into the T cell epitope at a position separated by at most 5 amino acids from the MHC-binding region (i.e. at most 5 amino acids may be between said cysteine and the terminal amino acid of the MHC-binding region), or said cysteine amino acid of (ii) may result from the mutation of a non-cysteine amino acid to a cysteine amino acid at a position separated by at most 5 amino acids from the MHC-binding region (i.e. at most 5 amino acids may be between said cysteine and the terminal amino acid of the MHC-binding region).

Furthermore, in the immunogenic peptides according to the invention, said cysteine amino acid of (ii) may be separated from the MHC-binding region of the T cell epitope by an artificial linker amino acid sequence of at most 5 amino acids (i.e. at most 5 amino acids may be between said cysteine and the terminal amino acid of the MHC-binding region). Apart from a peptide linker other organic compounds can be used as linker to link the parts of the immunogenic peptide to each other.

In any one of the immunogenic peptides according to the invention, said cysteine amino acid may be located N- or C-terminally adjacent to the MHC binding region.

In any one of the immunogenic peptides according to the invention, said disease-associated T cell epitope include a T cell epitope of an infectious agent, of a self antigen, of an allergen, of an allofactor or of an allograft antigen, and a T cell epitope specific or preferential to a tumor.

Any of the immunogenic peptides of the invention may further comprise an amino acid sequence (or another organic compound) facilitating uptake of the peptide into (late) endosomes for processing and presentation within MHC class II determinants. The immunogenic peptides according to the invention may thus further comprise, e.g., an endosomal targeting sequence. The late endosome targeting is mediated by signals present in the cytoplasmic tail of proteins and correspond to well-identified peptide motifs such as the dileucine-based [DE]XXXL[LI] or DXXLL motif (e.g. DXXXLL), the tyrosine-based YXXØ motif or the so-called acidic cluster motif. The symbol Ø represents amino acid residues with a bulky hydrophobic side chains such as Phe, Tyr and Trp. The late endosome targeting sequences allow for processing and efficient presentation of the antigen-derived T cell epitope by MHC-class II molecules. Such endosomal targeting sequences are contained, for example, within the gp75 protein (Vijayasaradhi et al. 1995, J Cell Biol 130, 807-820), the human CD3 gamma protein, the HLA-BM β (Copier et al. 1996, J Immunol 157, 1017-1027), the cytoplasmic tail of the DEC205 receptor (Mahnke et al. 2000, 7 Cell Biol 151, 673-683). Other examples of peptides which function as sorting signals to the endosome are disclosed in the review of Bonifacio and Traub (2003), Annu Rev Biochem 72, 395-447. Alternatively, the sequence can be that of a subdominant or minor T cell epitope from a protein, which facilitates uptake in late endosome without overcoming the T cell response towards the pathogen-associated derived T cell epitope., or the auto- or alloantigen derived T cell epitope.

Any of the above immunogenic peptides may be produced by chemical synthesis or by recombinant expression.

The invention further pertains to compositions comprising an immunogenic peptide according to the invention and further at least one of a solvent, diluent, carrier or adjuvant.

The present invention relates to the use of isolated immunogenic peptides for the prevention, treatment or suppression of infection in a subject by increasing the immune response towards specific antigens derived from an infectious agent used in a vaccination strategy. In particular, the immune response is the activation of CD4+ helper T cells and/or antibody response in said subject. In the above, said pathogen-associated antigen may be derived from viruses, bacteria or parasites. In particular, the invention provides ways to enhance, boost or augment the expansion and functional activity of effector CD4+ T cells, also referred to as helper CD4+ T cells. Such effector or helper CD4+ T cells belong to several subsets of cells defined according to their surface phenotype, production of cytokines and transcriptome. Thus, Th1, Th2, Th17 and Tfh cells have been delineated as representative of distinct effector subsets. In addition, Th9 cells have recently been described (for a review, see Locksley et al. 2009, J Exp Med 206, 1643-1646). In particular, the invention provides ways to expand specific CD4+ T helper cells. The result is a more efficient response towards pathogens including the production of higher antibody concentrations.

The present invention also relates to the use of isolated immunogenic peptides for the suppression of immune responses against allergens or autoantigens in a subject by increasing the regulatory T cell response specific for that allergen or autoantigen. It further relates to the use of isolated immunogenic peptides for the suppression of immune responses against alloantigens in a subject by increasing the regulatory T cell response specific for that alloantigen. In the above, said autoantigen or alloantigen include autoantigens associated with autoimmune diseases such as insulin-dependent diabetes mellitus, thyroiditis, multiple sclerosis, rheumatoid arthritis, and include alloantigens derived from major histocompatibility complexes (MHC) of class I or class II, minor histocompatibility antigens or tissue specific antigens. In case of the immune responses to alloantigens (synonym used herein: allofactor), the immune response may be neutralizing the allofactor's biological activity. An example of the latter includes the development of neutralizing antibodies in e.g. hemophiliacs to exogenous factor VIII. The present invention provides ways to prevent, treat or suppress, in a subject, autoimmune disease or graft rejection, or to prevent, treat or suppress, in a subject, an immune response that is neutralizing an allofactor (such as the blood clotting factor VIII to which recipients in need of it can mount an immune response that is neutralizing the administered factor VIII). In particular, the invention provides ways to augment the expansion and functional activity of regulatory CD4+ T cells. Such regulatory T cells belong to either the natural regulatory T cell population defined by expression of the Foxp3 transcription repressor or to one of the subsets of induced or adaptive regulatory T cells mainly defined by the production of suppressive cytokines such as IL-10 and TGF-beta (for a review, see Yi et al. 2006, Cell Mol Immunol 3, 189-195). In particular, the invention provides ways to expand specific CD4+ regulatory T cells. The result is a more efficient suppression of immune responses to autoantigens and reduced graft rejection rate.

The present invention also relates to the use of isolated immunogenic peptides for the treatment of a tumor in a subject by increasing the immune response towards tumor-specific antigens shed by the tumor in a vaccination strategy. In particular, the immune response is the activation of effector CD4+ T cell response in said subject. In the above, said tumor-derived antigen may be derived from oncogens or protooncogens, virus-derived proteins, surviving factors or clonotypic determinants. The present invention provides ways to prevent or suppress, in a subject, growth of a tumor or of cancer cells, or to treat a tumor or cancer. This also includes vaccination with the aim to prevent infection with tumor- or cancer-causing pathogens (e.g., certain strains of human papillomavirus). In particular, the invention provides ways to augment the expansion and functional activity of CD8+ T cells, via augmented or increased effector CD4+ T cell activation. In particular, the invention provides ways to expand specific CD8+ T cells. The result is a more efficient response towards tumor-derived antigens or antigens from tumor-causing pathogens, with higher activity of CD8+ T cells.

In any of the above "treatment" is to be understood to result in at least stabilization of the treated disease or disorder or to result in a partial or complete reversal of the disease or disorder towards a healthy condition. "Suppression" of a disease or disorder is to be understood to result in slower further development of said disease or disorder when compared to the average further development of said disease or disorder when left untreated. As the immunogenic peptides of the invention can be used in a vaccination approach, it follows that such peptides can be administered to a subject not yet displaying or suffering from a target disease or disorder, said administration with the aim to prevent said target disease or disorder to develop. Such prophylactic or prior immunization or prevention may completely block development of the target disease or disorder, or may prevent the target disease or disorder to develop towards an e.g. debilitating level. Prophylactic vaccination or immunization is particularly interesting in subjects at risk to develop a disease or disorder because of increased (risk of) exposure to e.g. a pathogen, because of hereditary or other predisposition, because of congenital defects, etc.

Examples of diseases in which an increased immune response by using the present invention is able to prevent, ameliorate or treat the disease are described hereunder. Antigens from which the T-cell epitope can be derived for use in the inventions are also exemplified.

vaccination against allergic diseases

The allergens that can be used for selection of T-cell epitopes are typically allergens which are selected from the group consisting of:
food allergens present in peanuts (Ara h1), fish (paralbumin) e.g. codfish, egg white (ovalbumin), crustacea e.g. shrimp (tropomyosin), milk (beta lactoglobulin) e.g. cow's milk, wheat (gluten), cereals, fruits of the Rosacea family (apple, plum, strawberry), vegetables of the Liliacea, Cruciferae, Solanaceae and Umbelliferae families, tree nuts, sesame, peanut, soybean and other legume family allergens, spices, melon, avocado, mango, fig, banana, among others.
house dust mites allergens obtained from *Dermatophagoides* spp or *D. pteronyssinus, D. farinae* and *D. microceras, Euroglyphus maynei* or *Blomia* sp.,
allergens from insects present in cockroach (Bla g2) or Hymenoptera,
allergens from pollen, especially pollens of tree, grass and weed,
allergens from animals, especially in cat (Fel d1), dog, horse and rodent (mus m1),
allergens from fungi, especially from *Aspergillus* (aspf1) *Alternaria* (Alt A6) or *Cladosporium* (cla h3),
occupational allergens present in products such as latex, amylase, etc.

vaccination against intra and extracellular pathogens

Intracellular pathogens are selected from the group consisting of any antigen derived from viruses, bacteria, mycobacteria or parasites with an intracellular life cycle. Viruses include ssDNA, dsDNA and RNA viruses, with as examples Herpesviridae, Flaviviridae and Picornaviridae, influenza, measles and immunodeficiency viruses. Bacteria and mycobacteria include *Mycobacterium tuberculosis*, other mycobacteria pathogenic for humans or animals, *Yersiniosis, Brucella, Chlamydiae, Mycoplasma, Rickettsiae, Salmonellae* and *Shigellae*. Parasites include *Plasmodiums, Leishmanias, Trypanosomas, Toxoplasma gondii, Listeria, Histoplasma*, among others.

Extracellular pathogens are selected from the group consisting of viruses, bacteria and parasites with a primarily extracellular life cycle and antigens to be used in the present invention can be derived therefrom.

vaccination against tumors

Example tumors which can be targeted by the products of the present invention and example associated antigens which can be used in the present invention are selected from the groups consisting of:
oncogenes, such as the MAGE identified in some melanomas;
proto-oncogenes, such as cyclin D1 expressed on soft tissues carcinomas such as those of the kidney or parathyroid, as well as in multiple myeloma;
virus-derived proteins, such as those from the Epstein-Barr virus in some carcinomas and in some Hodgkin-type lymphomas;
surviving factors, which are anti-apoptotic factors such as survivin or bcl2;
clonotypic determinants, such as idiotypic determinants derived from B cell receptor in follicular lymphomas or multiple myelomas or T cell receptor determinants in T cell malignancies.

Examples of diseases in which an increase tolerance by elicitation of regulatory T cells by using the present invention is able to prevent, ameliorate or treat the disease are described hereunder. Antigens from which the T-cell epitope can be derived for use in the inventions are also exemplified.

allergic disease as described above auto-immune diseases

Autoimmune diseases are selected from the group consisting of
(a) organ-specific diseases, such as Addison disease, hemolytic or pernicious anemia, Goodpasture syndrome, Graves disease, idiopathic thrombocytopenic purpura, insulin-dependent diabetes mellitus, juvenile diabetes, uveitis, Crohn's disease, ulcerative colitis, *pemphigus*, atopic dermatitis, autoimmune hepatitis, primary biliary cirrhosis, autoimmune pneumonitis, auto-immune carditis, myasthenia gravis, glomerulonephritis and spontaneous infertility);
(b) systemic diseases, such as lupus erythematosus, psoriasis, vasculitis, polymyositis, *scleroderma*, multiple sclerosis, ankylosing spondilytis, rheumatoid arthritis and Sjoegren syndrome). The autoimmune disorders are thus directed to own cells or tissues and include a reaction to "auto-antigens", meaning antigens (e.g. of proteins) that are own constituent parts of the specific mammalian organism. In this mechanism, auto-antigens are recognised by B- and/or T-cells which will install an immune reaction against said auto-antigen.
A non-limitative list of diseases encompassed by the term "auto-immune diseases" or "auto-immune disorders" comprises therefore Acute disseminated encephalomyelitis (ADEM), Addison's disease, Alopecia areata, Antiphospholipid antibody syndrome (APS), Autoimmune hemolytic anemia, Autoimmune hepatitis, Bullous pemphigoid, Behçet's disease, Coeliac disease, inflammatory bowel disease (IBD) (such as Crohns Disease and Ulcerative Colitis), Dermatomyositis, Diabetes mellitus type 1, Goodpasture's syndrome, Graves' disease, Guillain-Barré syndrome (GBS), Hashimoto's disease, Idiopathic thrombocytopenic purpura, Lupus erythematosus, Mixed Connective Tissue Disease, Multiple sclerosis (MS), Myasthenia gravis, Narcolepsy, *Pemphigus vulgaris*, Pernicious anaemia, Psoriasis, Psoriatic Arthritis, Polymyositis, Primary biliary cirrhosis, Rheumatoid arthritis (RA), Sjögren's syndrome, Temporal arteritis, Vasculitis, Wegener's granulomatosis and atopic dermatitis.

TABLE

Representative auto-antigens and diseases linked therewith

| Disease | antigen |
|---|---|
| thyroid diseases | thyroglobulin |
| | thyroid peroxidase |
| | TSH receptor |

TABLE-continued

Representative auto-antigens and diseases linked therewith

| Disease | antigen |
| --- | --- |
| type 1 diabetes | insulin (proinsulin) |
| | glutamic acid decarboxylase (GAD) |
| | tyrosine phosphatase IA-2 |
| | heat-shock protein HSP65 |
| | islet-specific glucose6-phosphatase catalytic subunit related protein (IGRP) |
| adrenalitis | 21-OH hydroxylase |
| polyendocrine syndromes | 17-alpha hydroxylase |
| | histidine decarboxylase |
| | tryptophan hydroxylase |
| | tyrosine hydroxylase |
| gastritis & pernicious anemia | H+/K+ ATPase intrinsic factor |
| multiple sclerosis | myelin oligodendrocyte glycoprotein (MOG) |
| | myelin basic protein (MBP) |
| | proteolipid protein (PLP) |
| myasthenia gravis | acetyl-choline receptor |
| ocular diseases | retinol-binding protein (RBP) |
| inner ear diseases | type II and type IX collagen |
| celiac disease | tissue transglutaminase |
| inflammatory bowel diseases | pANCA histone H1 protein |
| atherosclerosis | heat-shock protein HSP60 | transplantation

Alloantigens for use in the present invention are selected from the group deriving from:
- major histocompatibility complexes of class I or of class II
- minor histocompatiiblity complexes
- tissue-specific antigens
- immune response to allofactors Allofactors for use in the present invention are selected from the group consisting of:
- replacement therapy for coagulation defects or fibrinolytic defects, including factor VIII, factor IX and staphylokinase,
- hormones such as growth hormone or insulin,
- cytokines and growth factors, such as interferon-alpha, interferon-gamma, GM-CSF and G-CSF,
- antibodies for the modulation of immune responses, including anti-IgE antibodies in allergic diseases, anti-CD3 and anti-CD4 antibodies in graft rejection and a variety of autoimmune diseases, anti-CD20 antibodies in non-Hodgkin lymphomas, erythropoietin in renal insufficiency In any of the uses and methods described hereinabove, the immunogenic peptide according to the invention can be replaced by CD4+ effector T-cells primed with said immunogenic peptide, or can be replaced by a nucleotide sequence encoding the immunogenic peptide (e.g. in the form of naked DNA or a viral vector to be administered to an individual instead of the immunogenic peptide). In addition, a combination of multiple immunogenic peptides, i.e. more than 1 (e.g., 2, 3, 4, 5, 6, 7, 8, 9, 10 or more), can be used in any of the above.

The invention further encompasses isolated viral vectors characterized in that they are capable of expressing an immunogenic peptide according to the invention.

In any of the uses described hereinabove, said recipient is a mammal, in particular a (non-human) primate or a human.

Immunogenic peptides according to the invention can be generated starting from T cell epitope(s) of an antigen of interest. In particular, the T-cell epitope used may be a dominant T-cell epitope. The identification and selection of a T-cell epitope from an antigen of interest for use in the context of the present invention is within the knowledge of a person skilled in the art. For instance, peptide sequences isolated from an antigen of interest can be tested by, for example, T cell biology techniques, to determine whether the peptide sequences elicit a T cell response. Those peptide sequences found to elicit a T cell response are defined as having T cell stimulating activity. Human T cell stimulating activity can further be tested by culturing T cells obtained from an individual sensitized to an antigen of interest with a peptide/epitope derived from the antigen of interest, followed by determining whether proliferation of T cells occurs in response to the peptide/epitope as measured, e.g., by cellular uptake of tritiated thymidine. Stimulation indices for responses by T cells to peptides/epitopes can be calculated as the maximum CPM in response to a peptide/epitope divided by the control CPM. A T cell stimulation index (S.I.) equal to or greater than two times the background level is considered "positive." Positive results are used to calculate the mean stimulation index for each peptide/epitope for the group of peptides/epitopes tested. Non-natural (or modified) T-cell epitopes can further optionally be tested for their binding affinity to MHC class II molecules. The binding of non-natural (or modified) T-cell epitopes to MHC class II molecules can be performed in different ways. For instance, soluble HLA class II molecules are obtained by lysis of cells homozygous for a given class II molecule. The latter is purified by affinity chromatography. Soluble class II molecules are incubated with a biotin-labeled reference peptide produced according to its strong binding affinity for that class II molecule. Peptides to be assessed for class II binding are then incubated at different concentrations and their capacity to displace the reference peptide from its class II binding is calculated by addition of neutravidin. Methods can be found in for instance Texier et al. 2000, J Immunol 164, 3177-3184). The immunogenic peptides of the invention have a mean T cell stimulation index of greater than or equal to 2.0. An immunogenic peptide having a T cell stimulation index of greater than or equal to 2.0 is considered useful as a prophylactic or therapeutic agent. The immunogenic peptides according to the invention may have a mean T cell stimulation index of at least 2.5, at least 3.5, at least 4.0, or even at least 5.0. In addition, such peptides typically have a positivity index (P.I.) of at least about 100, at least 150, at least about 200 or at least about 250. The positivity index for a peptide is determined by multiplying the mean T cell stimulation index by the percent of individuals, in a population of individuals sensitive to an antigen of interest (e.g., at least 9 individuals, at least 16 individuals or at least 29 or 30, or even more), who have T cells that respond to the peptide (thus corresponding to the SI multiplied by the promiscuous nature of the peptide/epitope). Thus, the positivity index represents both the strength of a T cell response to a peptide (S.I.) and the frequency of a T cell response to a peptide in a population of individuals sensitive to an antigen of interest. In order to determine optimal T cell epitopes by, for example, fine mapping techniques, a peptide having T cell stimulating activity and thus comprising at least one T cell epitope as determined by T cell biology techniques is modified by addition or deletion of amino acid residues at either the N- or C-terminus of the peptide and tested to determine a change in T cell reactivity to the modified peptide. If two or more peptides which share an area of overlap in the native protein sequence are found to have human T cell stimulating activity, as determined by T cell biology techniques, additional peptides can be produced comprising all or a portion of such peptides and these additional peptides can be tested by a similar procedure. Following this technique, peptides are selected and produced recombinantly or synthetically. T cell epitopes or peptides are selected based on various factors, including the strength of the T cell response to the peptide/epitope (e.g., stimulation index) and the frequency of the T cell response to the peptide in a population of individuals.

Methods used for the identification of an antigen are known in the art. Thus, positional cloning or expression cloning strategies can be used to identify candidate antigens. For full description of the methodology, see for instance Mendoza et al. 1997, Immunity 7, 461-472. Alternatively, peptides actually presented by APC in either MHC class I or class II molecules can be eluted and separated by various chromatography methods. Full description of such methodology will be found in Scott et al. 2000, Immunity 12, 711-720. Candidate antigens can be screened by one or more in vitro algorithms to identify a T cell epitope sequence within an antigenic protein. Suitable algorithms include, but are not limited to those found on the following websites:

antigen.i2r.a-star.edu.sg/predBalbc/;
antigen.i2r.a-star.edu.sg/predBalbc/;
imtech.res.in/raghava/mhcbn/;
syfpeithi.de/home;
bs.informatik.uni-tuebingen.de/SVMHC;
bio.dfci.harvard.edu/Tools/antigenic
jenner.ac.uk/MHCPred/.

More details of these algorithms are described for example in Zhang et al. (2005) Nucleic Acids Res 15 33, W180-W183 (PREDBALB); Salomon & Flower (2006) BMC Bioinformatics 7, 501 (MHCBN); Schuler et al. (2007) Methods Mo/ Biol. 409, 75-93 (SYFPEITHI); Donnes & Kohlbacher (2006) Nucleic Acids Res. 34, W194-W197 (SVMHC); Kolaskar & Tongaonkar (1990) FEBS Lett. 276, 172-174 and Guan et al. (2003) Appl Bioinformatics 2, 63-66 (MHCPred).

More particularly, such algorithms allow the prediction within an antigenic protein of one or more nonapeptide sequences which will fit into the groove of an MHC II molecule.

The immunogenic peptides of the invention can be produced by recombinant expression in, e.g., bacterial cells (e.g. *Escherichia coli*), yeast cells (e.g., *Pichia* species, *Hansenula* species, *Saccharomyces* or *Schizosaccharomyces* species), insect cells (e.g. from *Spodoptera frugiperda* or *Trichoplusia ni*), plant cells or mammalian cells (e.g., CHO, COS cells). The construction of the therefore required suitable expression vectors (including further information such as promoter and termination sequences) involves meanwhile standard recombinant DNA techniques.

Recombinantly produced immunogenic peptides of the invention can be derived from a larger precursor protein, e.g., via enzymatic cleavage of enzyme cleavage sites inserted adjacent to the N- and/or C-terminus of the immunogenic peptide, followed by suitable purification.

In view of the limited length of the immunogenic peptides of the invention, they can be prepared by chemical peptide synthesis, wherein peptides are prepared by coupling the different amino acids to each other. Chemical synthesis is particularly suitable for the inclusion of e.g. D-amino acids, amino acids with non-naturally occurring side chains or natural amino acids with modified side chains such as methylated cysteine. Chemical peptide synthesis methods are well described and peptides can be ordered from companies such as Applied Biosystems and other companies. Peptide synthesis can be performed as either solid phase peptide synthesis (SPPS) or contrary to solution phase peptide synthesis. The best-known SPPS methods are t-Boc and Fmoc solid phase chemistry which is amply known to the skilled person. In addition, peptides can be linked to each other to form longer peptides using a ligation strategy (chemoselective coupling of two unprotected peptide fragments) as originally described by Kent (Schnolzer & Kent 1992, Int J Pept Prot Res 40, 180-193) and reviewed for example in Tam et al. 2001, Biopolymers 60, 194-205. This provides the tremendous potential to achieve protein synthesis which is beyond the scope of SPPS. Many proteins with the size of 100-300 residues have been synthesized successfully by this method. Synthetic peptides have continued to play an ever-increasing crucial role in the research fields of biochemistry, pharmacology, neurobiology, enzymology and molecular biology because of the enormous advances in the SPPS.

The physical and chemical properties of an immunogenic peptide of interest (e.g. solubility, stability) are examined to determine whether the peptide is/would be suitable for use in therapeutic compositions. Typically this is optimized by adjusting the sequence of the peptide. Optionally, the peptide can be modified after synthesis (chemical modifications e.g. adding/deleting functional groups) using techniques known in the art.

The invention further provides methods for generating antigen-specific effector CD4+ T cells, or antigen-specific regulatory T cells (Tregs or CD4+ regulatory T-cells), either in vivo or in vitro (ex vivo). The methods according to the invention have the advantage that higher numbers of either CD4+ effector T cells or CD4+ regulatory T cells are produced and that said cells can be generated which are specific for the antigen of interest.

Such methods include methods for obtaining a population of CD4+ effector cells with increased proliferative properties, said methods comprising the steps of:

providing peripheral blood cells;

contacting these cells with an immunogenic peptide according to the invention wherein the T cell antigen is derived from an infectious agent; and expanding these cells in the presence of IL-2

Such methods further include methods aimed at obtaining a population of CD4+ effector cells with increased proliferative properties, said methods comprising the steps of:

providing an immunogenic peptide according to the invention;

administering the immunogenic peptide to a subject wherein the T cell epitope is derived from an infectious agent; and obtaining a population of CD4+ effector cells with increased proliferative properties.

Such methods further include methods for obtaining a population of CD4+ regulatory cells with increased suppressive properties, said methods comprising the steps of:
- providing peripheral blood cells;
- contacting these cells with an immunogenic peptide according to the invention wherein the T cell epitope is derived from an auto- or alloantigen; and
- expanding these cells in the presence of IL-2

Such methods further include methods aimed at obtaining a population of CD4+ regulatory cells with increased suppressive properties, said methods comprising the steps of:
- providing an immunogenic peptide according to the invention wherein the T cell epitope is derived from an auto- or alloantigen;
- administering the immunogenic peptide to a subject; and
- obtaining a population of CD4+ regulatory cells with increased suppressive properties Such methods further include methods for obtaining a population of effector CD4+ T cells with increased proliferative properties, said methods comprising the steps of:
- providing peripheral blood cells;
- contacting these cells with an immunogenic peptide according to the invention wherein the T cell epitope is derived from a tumor-derived antigen; and
- expanding these cells in the presence of IL-2.

Such methods further include methods aimed at obtaining a population of effector CD4+ T cells with increased proliferative properties, said methods comprising the steps of:
- providing an immunogenic peptide according to the invention wherein the T cell epitope is derived from a tumor-derived antigen;
- administering the immunogenic peptide to a subject; and
- obtaining a population of effector CD4+ T cells with increased proliferative properties Populations of effector CD4+ T cells with increased proliferative properties and populations of CD4+ regulatory cells with increased suppressive properties obtainable by the above methods are also part of the invention, as well as their use for the manufacture of a medicament for treating a target disease or disorder.

For any of the above-described uses of the immunogenic peptides of the invention, said peptides can be replaced by antigen-specific effector CD4+ T cells, or by antigen-specific regulatory T cells. Both the use of allogeneic and autogeneic cells is envisaged. Any method comprising the administration of said antigen-specific effector CD4+ T cells or antigen-specific regulatory T cells to a subject in need is also known as adoptive cell therapy. Such therapy is of particular interest in case of treating acute episodes of a disease or disorder and in case of treating relapses of such disease or disorder. CD4+ effector T cells are crucial for prevention of infectious diseases such as viral, bacterial or parasitic diseases and are therefore of great potential. Their efficacy depends on antigenic specificity. CD4+ regulatory T cells are crucial in immunoregulation and have great therapeutic potential. The efficacy of regulatory T cell-based immunotherapy depends on the antigen specificity of the regulatory T cells. Moreover, the use of antigen-specific regulatory T cells as opposed to polyclonal expanded regulatory T cells reduces the total number of regulatory T cells required for therapy. CD4+ effector T cells are crucial for the treatment of tumors such as those expressing oncogens, protooncogens, virus-derived proteins, surviving factors or clonotypic determinants.

The present invention also relates to nucleic acid sequences encoding the immunogenic peptides of the present invention and methods for their use, e.g., for recombinant expression or in gene therapy. In particular, said nucleic acid sequences are capable of expressing an immunogenic peptides of the invention.

The immunogenic peptides of the invention may indeed be administered to a subject in need by using any suitable gene therapy method. Immunization with an immunogenic peptide of the invention, immunization by using suitable gene therapy and adoptive cell transfer may be combined. When combined, said immunization, adoptive cell transfer and gene therapy can be used concurrently or sequentially in any possible combination.

In gene therapy, recombinant nucleic acid molecules encoding the immunogenic peptides can be used as naked DNA or in liposomes or other lipid systems for delivery to target cells. Other methods for the direct transfer of plasmid DNA into cells are well known to those skilled in the art for use in human gene therapy and involve targeting the DNA to receptors on cells by complexing the plasmid DNA to proteins. In its simplest form, gene transfer can be performed by simply injecting minute amounts of DNA into the nucleus of a cell, through a process of microinjection. Once recombinant genes are introduced into a cell, they can be recognized by the cells normal mechanisms for transcription and translation, and a gene product will be expressed. Other methods have also been attempted for introducing DNA into larger numbers of cells. These methods include: transfection, wherein DNA is precipitated with calcium phosphate and taken into cells by pinocytosis; electroporation, wherein cells are exposed to large voltage pulses to introduce holes into the membrane); lipofection/liposome fusion, wherein DNA is packed into lipophilic vesicles which fuse with a target cell; and particle bombardment using DNA bound to small projectiles. Another method for introducing DNA into cells is to couple the DNA to chemically modified proteins. Adenovirus proteins are capable of destabilizing endosomes and enhancing the uptake of DNA into cells. Mixing adenovirus to solutions containing DNA complexes, or the binding of DNA to polylysine covalently attached to adenovirus using protein crosslinking agents substantially improves the uptake and expression of the recombinant gene. Adeno-associated virus vectors may also be used for gene delivery into vascular cells. As used herein, "gene transfer" means the process of introducing a foreign nucleic acid molecule into a cell, which is commonly performed to enable the expression of a particular product encoded by the gene. The said product may include a protein, polypeptide, anti-sense DNA or RNA, or enzymatically active RNA. Gene transfer can be performed in cultured cells or by direct administration into mammals. In another embodiment, a vector comprising a nucleic acid molecule sequence encoding an immunogenic peptide according to the invention is provided. In particular embodiments, the vector is generated such that the nucleic acid molecule sequence is expressed only in a specific tissue. Methods of achieving tissue-specific gene expression are well known in the art, e.g., by placing the sequence encoding an immunogenic peptide of the invention under control of a promoter, which directs expression of the peptide specifically in one or more tissue(s) or organ(s). Expression vectors derived from viruses such as retroviruses, vaccinia virus, adenovirus, adeno-associated virus, herpes viruses, RNA viruses or bovine papilloma virus, may be used for delivery of nucleotide sequences (e.g., cDNA) encoding peptides, homologues or derivatives thereof according to the invention into the targeted tissues or cell population. Methods which are well known to those skilled in the art can be used to construct recombinant viral vectors containing such coding sequences. Alternatively, engineered cells containing a nucleic acid molecule coding for an immunogenic peptide according to the invention may be used in gene therapy.

Viral vectors for the purpose of gene therapy or gene vaccination are highly amenable to modifications by means of recombinant nucleic acid technology. In view of the above, a skilled person will further easily envisage that the modification to the viral vector T-cell epitope as applied in the immunogenic peptides and their uses according to the invention can be introduced immediately in the viral vector itself. Hence, the invention further encompasses modified viral vectors defined as isolated viral vectors characterized in that at least one T-cell epitope present in at least one of the viral vector proteins is modified by introducing a cysteine residue as described for the immunogenic peptides according to the invention. In one embodiment thereto, said viral vector is further characterized in that said modified T-cell epitope is capable of being presented by an MHC class II determinant. In another embodiment, said isolated viral vectors are further characterized in that their cell transducing properties are not significantly altered compared to the same viral vector not carrying the T-cell epitope modification.

Where the administration of one or more peptides according to the invention is ensured through gene transfer (i.e. the administration of a nucleic acid which ensures expression of peptides according to the invention in vivo upon administration), the appropriate dosage of the nucleic acid can be determined based on the amount of peptide expressed as a result of the introduced nucleic acid.

The medicament of the invention is usually, but not necessarily, a (pharmaceutical) formulation comprising as active ingredient at least one of the immunogenic peptides of the invention, a (population of) CD4+ effector T cells or a (population of) CD4+ regulatory T cells specific for said immunogenic peptide or a gene therapeutic vector capable of expressing said immunogenic peptide. Apart from the active ingredient(s), such formulation will comprise at least one of a (pharmaceutically acceptable) diluent, solvent, carrier or adjuvant. Typically, pharmaceutically acceptable compounds (such as diluents, solvents, carriers and adjuvants) can be found in, e.g., a Pharmacopeia handbook (e.g. US-, European- or International Pharmacopeia). The medicament or pharmaceutical composition of the invention normally comprises a (prophylactically or therapeutically) effective amount of the active ingredient(s) wherein the effectiveness is relative to the condition or disorder to be prevented or treated. In particular, the pharmaceutical compositions of the invention are vaccines for prophylactic or therapeutic application.

The medicament or pharmaceutical composition of the invention may need to be administered to a subject in need as part of a prophylactic or therapeutic regimen comprising multiple administrations of said medicament or composition. Said multiple administrations usual occur sequentially and the time-interval between two administrations can vary and will be adjusted to the nature of the active ingredient and the nature of the condition to be prevented or treated. The amount of active ingredient given to a subject in need in a single administration can also vary and will depend on factors such as the physical status of the subject (e.g., weight, age), the status of the condition to be prevented or treated, and the experience of the treating doctor, physician or nurse.

The term "diluents" refers for instance to physiological saline solutions. The term "adjuvant" usually refers to a pharmacological or immunological agent that modifies (preferably increases) the effect of other agents (e.g., drugs, vaccines) while having few if any direct effects when given by themselves. As one example of an adjuvant aluminum hydroxide (alum) is given, to which an immunogenic peptide of the invention can be adsorbed. Further, many other adjuvants are known in the art and can be used provided they facilitate peptide presentation in MHC-class II presentation and T cell activation. The term "pharmaceutically acceptable carrier" means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. They include any and all solvents, dispersion media, coatings, antibacterial and antifungal agents (for example phenol, sorbic acid, chlorobutanol), isotonic agents (such as sugars or sodium chloride) and the like. Additional ingredients may be included in order to control the duration of action of the active ingredient in the composition. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders. Suitable pharmaceutical carriers for use in said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. They may also be prepared by micronisation, for instance in view to obtain them in the form of microspheres usually having a diameter of about 1 to 10 μm, namely for the manufacture of microcapsules for controlled or sustained release of the active ingredients.

Immunogenic peptides, homologues or derivatives thereof according to the invention (and their physiologically acceptable salts or pharmaceutical compositions all included in the term "active ingredients") may be administered by any route appropriate to the condition to be prevented or treated and appropriate for the compounds, here the immunogenic proteins to be administered. Possible routes include regional, systemic, oral (solid form or inhalation), rectal, nasal, topical (including ocular, buccal and sublingual), vaginal and parenteral (including subcutaneous, intramuscular, intravenous, intradermal, intraarterial, intrathecal and epidural). The preferred route of administration may vary with for example the condition of the recipient or with the condition to be prevented or treated.

The formulations may conveniently be presented in unit dosage form and may be prepared by any of the methods well known in the art of pharmacy. Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste. A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

The present invention will now be illustrated by means of the following example, which is provided without any limiting intention. Furthermore, all references described herein are explicitly included herein by reference.

EXAMPLES

Example 1

The house dust mite-derived allergen Der p2 is a 14 kD non-glycosylated protein containing a H-2b or H-2d restricted MHC class II epitope or sequence EPCIIHRGKPF (SEQ ID NO:1; amino acid residues 25-35 of Der p2) in which E corresponds to the first anchoring residue. Amino-terminal end flanking residues, of sequence CHGS (SEQ ID NO:2; amino acid residues 21-24 of Der p2), encompasses a monocysteinic glutaredoxin motif.

To determine whether the cysteine residue positioned in P(−4) increased the proliferative response of specific CD4+ effector T cells upon cognate interaction with antigen-presenting cells loaded with a peptide encompassing amino acids CHGSEPCIIHRGKPF (amino acid residues flanking the MHC binding site are underlined) (SEQ ID NO:3), each of the 4 amino acid residues of the flanking sequence was substituted into alanine.

T cell-depleted mitomycin C-treated splenocytes from naïve BALB/c mice were used as antigen-presenting cells and loaded with various mutant peptides (0.1 μM). The p21-35 (SEQ ID NO:3)-specific CD4+ T cell clone was then added to the culture for a 48-h incubation, after which $^3$H-thymidine was added and its incorporation measured after an additional 18 h of culture. Results are shown in FIG. 1 as percentage of incorporation obtained by comparison with p21-35 wildtype sequence (SEQ ID NO:3). It shows that substitution of cysteine in P(−4) by alanine (peptide of SEQ ID NO:4: AHGSEPCIIHRGKPF) reduced by 70% the proliferative response of the specific T cell clone. Data are representative of three independent experiments.

Example 2

The NPM-ALK chimeric gene encodes a constitutively activated tyrosine kinase that has been shown to be a potent oncogene. This fusion gene is composed of nucleophosmin (NPM) and a novel receptor tyrosine kinase gene, named anaplastic lymphoma kinase (ALK). Lymphoma cell lines derived from mouse strains made transgenic for the NPM-ALK fusion protein exhibit oncogenic properties. When inoculated in immunocompetent recipient, such cells develop aggressive tumors. Phenotypic assessment of such tumor cell lines show that they do not express class II major histocompatibility determinants, but are positive for class I MHC determinants.

C57BL/6 mice were inoculated by subcutaneous injection of NPM-ALK tumor cells ($2\times10^6$ tumor cells (R80 NPM-ALK cells, H-2b-restricted) suspended in 100 μl PBS and injected subcutaneously in the flank 10 days after the last peptide injection and the growth of the tumor was evaluated with a caliper. Usually, such mice develop tumors within 5-6 days, which then grow to reach a diameter of ±12 mm within 3 weeks. C57BL/6 mice were immunized before inoculation of tumor cells by 50 μg of a peptide of sequence YCT QDPDVINTA (SEQ ID NO:5), 4 times and at an interval of 10 days; the peptide was adsorbed on an alum (alhydrogel) carrier. This MHC class II-restricted epitope is a contiguous part of the ALK protein and corresponds to amino acids 1385-1396 of the ALK protein as given in GenBank Accession Number Q9UM73 (version Q9UM73.2). Tumor cells were inoculated 10 days after the last immunization. Tumor growth was followed in preimmunized mice and compared to that of a control group, which was not preimmunized. The results presented in FIG. 2 show that tumor growth was very much reduced in preimmunized mice. The peptide of sequence YCTQDPDVINTA (SEQ ID NO:5) was demonstrated to boost the activation of ALK-specific CD4+ T cells. The difference between groups was highly significant at day 20 ($p<0.008$), as evaluated by a Mann-Whitney U test.

Example 3

*Mycobacterium tuberculosis*

*Mycobacterium tuberculosis* is responsible for thousands of deaths every year. The only available vaccination, the Calmette-Guérin *Mycobacterium bovis*-based vaccine (BCG), is not efficient. In addition, several *Mycobacterium* strains show resistance to conventional chemotherapy. Antigen-specific CD4+ cells are known to occur in tuberculosis (Winslow et al. (2003) J. Immunol. 170: 2046-2052), which can be protective (Khader et al. (2007) Nature Immunol. 8:369-377).

*M. tuberculosis* produces a number of antigens that are presented by both MHC class I and MHC class II determinants. Antigens presented by class I determinants are recognized by CD8+ T lymphocytes, which carry a cytolytic activity aimed at eliminating cells infected with *M. tuberculosis*. However, in chronic carrier patients, this mechanism is not efficient enough to eliminate infected cells.

CD8+ T cells require help from other lymphocyte subsets and in particular cells belonging to the CD4+ lineage. Activation of CD4+ T cells leads to production of IL-2, which is providing the necessary signal for CD8+ T cells to acquire full cytolytic potential. A therapeutic strategy by which specific CD4+ T cells would be activated would therefore be of benefit in the CD8+ T cell-dependent elimination of *M. tuberculosis* infected cells.

One of the best candidate antigen for such purpose is antigen 85b (Ag85b), a protein produced by intracellular *M. tuberculosis*. A dominant T cell epitope corresponding to the amino acid sequence 266 to 275 has been mapped. The full sequence of such epitope is YWGAQLNAM (SEQ ID NO:6).

Examination of flanking residues in both amino and carboxyterminal ends of SEQ ID NO:6 identified no cysteine within a length of 6 amino acids. A cysteine residue was added in position P-4 at the amino terminal end of the peptide, which generated a modified T-cell epitope with sequence: CSWE YWGAQLNAM (SEQ ID NO:7; cysteine underlined and preceding amino acids 163-275 of the Ag85b antigen).

C57BL/6 mice are immunized with the peptide of SEQ ID NO:7 together with an adjuvant such as alum. Three injections of 50 μg of the peptide are made at fortnight intervals. Two weeks after the last immunization, mice are sacrificed and CD4+ T lymphocytes prepared from the spleen by a combination of density gradient centrifugation and selection on antibody-coated magnetic beads. CD4+ T cells are then activated and expanded in vitro using antigen-presenting cells loaded with peptide of SEQ ID NO:7, and cloned by limiting dilution.

For control experiments, C57BL/6 mice are immunized with peptide of SEQ ID NO:6. CD4+ T cells are obtained from the spleen as described above, using a combination of selection steps with antibody-coated magnetic beads.

To obtain a source of specific CD8+ T cells, C57BL/6 mice are immunized with recombinant Ag85b and CD8+ T cells are prepared from the spleen as described above, using magnetic beads loaded with an anti-CD8+ antibody.

Macrophages obtained from C57BL/6 mice are incubated with Ag85b for 60 minutes at 37° C. and overnight at 4° C. for uptake of the protein and presentation in both class I and class II MHC determinants. Such macrophages are further incubated with $^{51}$Cr for evaluation of the CD8 T cell-dependent killing of macrophages, using a chrome release assay.

To test the capacity of CD4+ T cells to activate CD8+ T cells for macrophage lysis, the following experiment is carried out. In cultures of $^{51}$Cr labeled macrophages presenting Ag85b derived epitopes, CD4+ T cells obtained as described above from mice injected with peptide of SEQ ID NO:7 are added together with a population of CD8+ T cells obtained from mice immunized with Ag85b. As a control experiment, CD4+ T cells obtained from mice immunized with peptide of SEQ ID NO:6 are incubated with macrophages and CD8+ obtained from animals immunized with Ag85b.

It can be seen that a significant degree of macrophage lysis (as measured by $^{51}$Cr release) is obtained when CD4+ T cells obtained from mice immunized with peptide of SEQ ID NO:7 but not with CD4+ elicited by peptide of SEQ ID NO:6 immunization.

It is therefore concluded that the presence of a cysteine in the flanking regions of a class II-restricted T cell epitope is sufficient to enforce the killing of macrophages presenting Ag85b derived T cell epitopes. This killing is exerted by highly activated CD8+ T cells.

Example 4

Influenza Virus

The influenza virus, like any other virus, is an obligate intracellular pathogen. It is well known to affect people by the millions every year for reasons which are related to its high degree of contagiousness and capacity to mutate rapidly, rendering acquired immunity inefficient from one year to the other. The virus carries a very significant morbidity and mortality. Current vaccination strategies make use of surface proteins such as hemagglutinin and neuraminidase, which induce high titres of specific antibodies but are rather inefficient at eliciting cytolytic T cells that would eliminate infected cells.

The hemagglutinin antigen carries a number of T cell epitopes that are presented in the context of MHC-class II determinants and activate effector T cells, which provide help for the production of specific antibodies. Class I-restricted T cell epitopes are also produced with elicitation of CD8+ T cells. However, the cytolytic activity of CD8+ T cells on infected cells is insufficient to eliminate the spreading of infection through the body. A method by which the activity of cytotoxic CD8+ T cells could be increased would be of benefit for the prevention and cure of influenza infection.

Thus the peptide YSTVASSLV (SEQ ID NO:8; amino acids 534-542 of the hemagglutinin precursor amino acid sequence of e.g. GenBank accession number AF408859_1) encompasses a class II restricted T cell epitope from the H1N9 influenza virus. Examination of the sequence of flanking residues shows that no cysteine residues are located within flanking regions up to 6 amino acids in either amino- or carboxy-terminal end.

A synthetic peptide was produced containing a cysteine residue in position P-4, with sequence CLAI YSTVASSLV LLV (SEQ ID NO:9; cysteine underlined and preceding amino acids 531-545 of the hemagglutinin precursor amino acid sequence of e.g. GenBank accession number AF408859_1), which also contains 3 amino acids of the carboxy-terminal end-flanking region.

Peptides of SEQ ID NO:9 and of SEQ ID NO:8 were used for immunizing C57BL/6 mice using the same protocol as described in example 3 in order to obtain populations of specific CD4+ T cells.

A group of C57BL/6 mice are immunized with recombinant hemagglutinin of H1N9 influenza virus in order to obtain a source of specific CD8+ T cells, as described in example 3.

CD4+ T cells were prepared from the spleen of each group of mice immunized with either peptides of SEQ ID NO:8 or SEQ ID NO:9.

Dendritic cells were loaded with recombinant hemagglutinin of H1N9 influenza virus for presentation of epitopes in both class I and class II determinants. Cultures of loaded dendritic cells were also incubated with $^{51}$Cr as a marker for dendritic cell lysis (chrome release assay).

Incubation of such dendritic cells with CD4+ T cells from mice immunized with peptide of SEQ ID NO9 together with CD8+ T cells prepared from mice immunized with hemagglutinin induced significant lysis of hemagglutinin-loaded dendritic cells, whilst experiments carried out with CD4+ T cells obtained after immunization with peptide of SEQ ID NO:8 show no lysis. Omitting CD8+ T cells in the culture completely suppresses dendritic cell cytolysis, indicating that lysis was mediated by activated CD8+ T cells.

Thus, introduction of a single cysteine residue within the flanking regions of a class II restricted T cell epitope is sufficient to boost the activation of CD8+ T cells resulting in significant lysis of the target cell.

Example 5

Anti-Allofactor Antibodies

Administration of a therapeutic protein (called allofactor in the present example) is common practice in medicine. One example is the administration of factor VIII of the coagulation pathway in hemophilia A patients. Unfortunately, on many occasions, such administration results in the elicitation of antibodies which recognize and neutralize the activity of the therapeutic protein. In hemophilia A, about 30% of patients treated by infusions of factor VIII develop antibodies inhibiting the procoagulant activity of factor VIII.

It is therefore advantageous to have a method by which undesirable anti-allofactor antibodies could be specifically eliminated.

The BO2C11 antibody is a human monoclonal antibody which inhibits the function of factor VIII by binding to the C2 domain and thereby prevent the binding of factor VIII to phospholipids (Jacquemin et al. (1998) Blood 92: 496-506). The sequence of the variable part of the heavy chain (VH region) of BO2CII contains a class II restricted T cell epitope which is overlapping with the complementarity determining region 3 (CDR 3). Raising antibodies to BO2C11 by eliciting CD4+ T cells recognizing such epitope would constitute a specific method to eliminate BO2C11 antibodies, both by forming complexes with circulating BO2C11 and by suppressing the production of BO2C11 antibodies at the level of the B cell receptor.

The sequence YCAVPDPDA (SEQ ID NO:10; corresponding to amino acids 114-122 of the amino acid sequence of GenBank accession number CAA11829) encompasses a class II restricted T cell epitope located in the CDR3 region of BO2C11 VH region. Examination of the amino acid sequence at both amino- and carboxyterminal ends of this epitope identified no cysteine within 6 amino acids. A peptide was produced in which a cysteine residue was added in position P-4, giving the sequence CAVY YCAVPDPDA FDI (SEQ ID NO:11; cysteine underlined and preceding amino acids 111-125 of the amino acid sequence of GenBank accession number CAA11829) including 3 amino acids of the natural flanking sequence of the carboxy-terminal end.

A mouse strain was created which expresses the BO2C11 molecule as a B cell receptor. Such mice were immunized with peptides of SEQ ID NO:11 adsorbed on alum, using 50 μg on 4 occasions at 10-day intervals. Mice were then bled and tested for the presence of antibodies recognizing the peptide of SEQ ID NO:10 and the BO2C11 antibody, as assess by direct binding ELISA. High concentrations of antibodies to either the peptide of SEQ ID 10 or to the BO2C11 antibody are detected.

Furthermore, the presence of the BO2C11 BCR on circulating, splenic and bone marrow B cells was evaluated by FACS using an anti-human Fc-gamma antibody. It is shown that mice immunized with peptide of SEQ ID 11 have no B cells expressing the transgenic BCR in either circulation, spleen or bone marrow.

It was concluded that administration of a peptide encompassing a class II restricted T cell epitope derived from the VH region of an antibody, and containing a cysteine within the flanking residues, results in the elimination of the target antibody and of B cells producing such antibody.

Example 6

Anti-T Cell Receptor Antibodies

Pathogenic CD4+ T cells are considered as key elements in a number of pathologies, including allergic and autoimmune diseases. Such cells produce cytokines for helping B cells to produce antibodies and provide help to CD8+ T cells for full activation and acquisition of effector functions. A method by which it would be feasible to eliminate specifically pathogenic CD4+ T cells would therefore be highly desirable.

The alpha-beta T cell receptor (TCR) of CD4+ T cells contains variable parts within heavy and light chains. Such variable parts encompass class II restricted T cell epitopes, which can be used within the scope of the present invention.

The clone G121 is a CD4+ T cell generated towards allergen Der p 2 of *Dermatophagus pteronyssinus*. The VH region of the TCR contains a class II restricted T cell epitope of sequence: VYFCASSER (SEQ ID NO:12) corresponding to amino acids 106 to 114 of the G121 TCR VH region. This sequence contains 5 amino acids at the carboxyterminal end which belong to the CDR 3 region of the VH.

Examination of the sequence of flanking residues identified no cysteine within the 6 amino acid sequence on either amino- or carboxyterminal end of the epitope. A peptide was produced in which a cysteine residue was added in position P-4, giving the sequence CQTA VYFCASSER TGG (SEQ ID NO:13, cysteine underlined) including 3 amino acids of the natural flanking sequence of the carboxy-terminal end. BALB/c mice were immunized with peptide of SEQ ID NO13 as described in example 5 for antibody-derived T cell epitopes. The G121 CD4+ T cell clone was labeled with CFSE and administered to immunized mice by injecting 200,000 cells per mouse in the tail vein. One day after cell administration, mice were killed and the presence of the CFSE-labeled G121 clone was detected in peripheral blood and spleen by FACS analysis. It is shown that mice immunized with peptide of SEQ ID NO:13 have no residual G121 cells in either the peripheral blood or the spleen. Control experiments carried out with non-immunized mice show CFSE-labeled G121 cells in the spleen. Additionally, the serum of immunized mice contains antibodies to G121 TCR, as identified by Facs analysis in which G121 cells are first incubated with a dilution of the serum of mice immunized with peptide of SEQ ID NO13, washed and further incubated with FITC-labeled anti-mouse Fcgamma antibody.

It is concluded that immunization with a peptide encompassing a class II restricted T cell epitope located in the variable region of the TCR elicits an antibody response which is sufficient to eliminate the cell carrying the corresponding epitope, namely the G121 clone.

Example 7

ALK+ Tumors

Experiments reported in example 2 indicate that direct immunization of mice with a peptide encompassing a class II-restricted epitope of ALK containing a single cysteine in flanking residues resulted in significant delay in tumor growth and reduction of tumor size. Peptide of SEQ ID NO:5 elicited increased activation properties on class II-restricted CD4+ T cells. The in vivo effect of such preimmunization was attributed to the elicitation of CD8+ T cells with cytolytic properties for tumor cells. It is well known in the art that CD8+ T cell require help provided by CD4+ T cells to acquire full effector properties.

To confirm that increased specific CD4+ T cell activation was the primary effect resulting from immunization with epitopes containing a single cysteine in flanking residues (as exemplified by peptide of SEQ ID NO:5), we set up an in vitro experiment in which naïve CD4+ T cells were converted into potent effector cells by exposure to a class II-restricted epitope of ALK.

Thus, naïve CD4+ T cells were isolated form the spleen of C57BL/6 mice using magnetic beads sorting. Cells were incubated with syngeneic dendritic cells loaded with either a peptide of sequence GAA EGG WTGPGAGPR (SEQ ID NO:14), corresponding to aminoacids 1541-1555 of the ALK protein in its natural or wildtype (wt in the figure) sequence or with a peptide of sequence CGG WTGP- GAGPR (SEQ ID NO:15), in which a single cysteine was added at position 1544 of the ALK protein.

After four cycles of stimulation using 20 μg of either peptide, cells were washed and added at a 5/1 ratio to T-cell deprived splenocytes used as antigen-presenting cells and loaded with either 1 μM or 10 μM of peptide of SEQ ID NO:14.

FIG. 3 indicates that the proliferation rate of CD4+ T cells, as assessed by incorporation of tritiated thymidine was significantly increased when a peptide containing a single cysteine (SEQ ID NO:15) was used to stimulate CD4+ T cells.

The following sequences have been disclosed in the present application and are incorporated in the sequence listing:

SEQ ID NO: 1
Glu Pro Cys Ile Ile His Arg Gly Lys Pro Phe

SEQ ID NO: 2
Cys His Gly Ser

SEQ ID NO: 3
Cys His Gly Ser Glu Pro Cys Ile Ile His Arg Gly Lys Pro Phe

SEQ ID NO: 4
Ala His Gly Ser Glu Pro Cys Ile Ile His Arg Gly Lys Pro Phe

SEQ ID NO: 5
Tyr Cys Thr Gln Asp Pro Asp Val Ile Asn Thr Ala

SEQ ID NO: 6
Tyr Trp Gly Ala Gln Leu Asn Ala Met

SEQ ID NO: 7
Cys Ser Trp Glu Tyr Trp Gly Ala Gln Leu Asn Ala Met

SEQ ID NO: 8
Tyr Ser Thr Val Ala Ser Ser Leu Val

SEQ ID NO: 9
Cys Leu Ala Ile Tyr Ser Thr Val Ala Ser Ser Leu Val Leu Val

SEQ ID NO: 10
Tyr Cys Ala Val Pro Asp Pro Asp Ala

SEQ ID NO: 11
Cys Ala Val Tyr Tyr Cys Ala Val Pro Asp Pro Asp Ala Phe Asp Ile

SEQ ID NO: 12
Val Tyr Phe Cys Ala Ser Ser Glu Arg

SEQ ID NO: 13
Cys Gln Thr Ala Val Tyr Phe Cys Ala Ser Ser Glu Arg Thr Gly Gly

SEQ ID NO: 14
Gly Ala Ala Glu Gly Gly Trp Thr Gly Pro Gly Ala Gly Pro Arg

SEQ ID NO: 15
Cys Gly Gly Trp Thr Gly Pro Gly Ala Gly Pro Arg

---

The invention claimed is:

1. A unit dosage form comprising an active ingredient consisting of an isolated peptide with a length of between 9 and 30 amino acids, wherein said peptide consists of:
   a) a natural MHC class II T cell epitope of a protein, said epitope comprising an 8 or 9 amino acid sequence that is capable of binding into the cleft of a human MHC class II molecule, and
   b) an amino acid or a sequence of between 2 and 6 amino acids at the n-terminal and/or c-terminal side of the MHC class II T cell epitope of a), comprising a reducing cysteine residue separated by at most 5 amino acids from the n-terminal and/or c-terminal end, respectively, of the 8 or 9 amino acid sequence that is capable of binding into the cleft of the human MHC class II molecule, wherein said cysteine residue does not occur as part of a cysteine disulfide bridge,
   wherein said amino acid or said sequence of between 2 and 6 amino acids does not comprise a C-xx-[CST] or [CST]-xx-C redox motif sequence,
   wherein said cysteine residue does not occur in a sequence with the motif C-xx-[CST] or [CST]-xx-C, and
   wherein said isolated peptide is an artificial peptide wherein the sequence defined in part a) and b) differs from the sequence as occurring in the wild type sequence of said protein.

2. The unit dosage form according to claim 1, wherein the amino acid or the sequence of between 2 and 6 amino acids defined in part b) contains only one cysteine.

3. The unit dosage form according to claim 1, wherein said peptide has a length of between 9 and 20 amino acids.

* * * * *

SEQUENCE LISTING

<160> NUMBER OF SEQ ID NOS: 15

<210> SEQ ID NO 1
<211> LENGTH: 11
<212> TYPE: PRT
<213> ORGANISM: Dermatophagoides pteronyssinus

<400> SEQUENCE: 1

Glu Pro Cys Ile Ile His Arg Gly Lys Pro Phe
1               5                   10

<210> SEQ ID NO 2
<211> LENGTH: 4
<212> TYPE: PRT
<213> ORGANISM: Dermatophagoides pteronyssinus

<400> SEQUENCE: 2

Cys His Gly Ser
1

<210> SEQ ID NO 3
<211> LENGTH: 15
<212> TYPE: PRT
<213> ORGANISM: Dermatophagoides pteronyssinus

<400> SEQUENCE: 3

Cys His Gly Ser Glu Pro Cys Ile Ile His Arg Gly Lys Pro Phe
1               5                   10                  15

```
<210> SEQ ID NO 4
<211> LENGTH: 15
<212> TYPE: PRT
<213> ORGANISM: artificial sequence
<220> FEATURE:
<223> OTHER INFORMATION: synthetic peptide; Der p2 amino acids 21-35
      with mutation c21A

<400> SEQUENCE: 4

Ala His Gly Ser Glu Pro Cys Ile Ile His Arg Gly Lys Pro Phe
1               5                   10                  15

<210> SEQ ID NO 5
<211> LENGTH: 12
<212> TYPE: PRT
<213> ORGANISM: artificial sequence
<220> FEATURE:
<223> OTHER INFORMATION: synthetic peptide; ALK-epitope

<400> SEQUENCE: 5

Tyr Cys Thr Gln Asp Pro Asp Val Ile Asn Thr Ala
1               5                   10

<210> SEQ ID NO 6
<211> LENGTH: 9
<212> TYPE: PRT
<213> ORGANISM: artificial sequence
<220> FEATURE:
<223> OTHER INFORMATION: synthetic peptide; Mycobacterium tuberculosis
      Ag85b, amino acids 266-275

<400> SEQUENCE: 6

Tyr Trp Gly Ala Gln Leu Asn Ala Met
1               5

<210> SEQ ID NO 7
<211> LENGTH: 13
<212> TYPE: PRT
<213> ORGANISM: artificial sequence
<220> FEATURE:
<223> OTHER INFORMATION: synthetic peptide; Mycobacterium tuberculosis
      Ag85b, amino acids 263-275 preceded by cysteine

<400> SEQUENCE: 7

Cys Ser Trp Glu Tyr Trp Gly Ala Gln Leu Asn Ala Met
1               5                   10

<210> SEQ ID NO 8
<211> LENGTH: 9
<212> TYPE: PRT
<213> ORGANISM: artificial sequence
<220> FEATURE:
<223> OTHER INFORMATION: synthetic peptide; influenza virus H1N9, amino
      acids 534-542 of hemagglutinin precursor

<400> SEQUENCE: 8

Tyr Ser Thr Val Ala Ser Ser Leu Val
1               5

<210> SEQ ID NO 9
<211> LENGTH: 16
<212> TYPE: PRT
<213> ORGANISM: artificial sequence
<220> FEATURE:
<223> OTHER INFORMATION: synthetic peptide; influenza virus H1N9, amino
      acids 534-542 of hemagglutinin precursor preceded by cysteine

<400> SEQUENCE: 9
```

```
Cys Leu Ala Ile Tyr Ser Thr Val Ala Ser Ser Leu Val Leu Leu Val
1               5                   10                  15
```

<210> SEQ ID NO 10
<211> LENGTH: 9
<212> TYPE: PRT
<213> ORGANISM: artificial sequence
<220> FEATURE:
<223> OTHER INFORMATION: synthetic peptide; amino acids 114-122 of vh
      (CDR3) of human anti-factor VIII antibody B02C11

<400> SEQUENCE: 10

```
Tyr Cys Ala Val Pro Asp Pro Asp Ala
1               5
```

<210> SEQ ID NO 11
<211> LENGTH: 16
<212> TYPE: PRT
<213> ORGANISM: artificial sequence
<220> FEATURE:
<223> OTHER INFORMATION: synthetic peptide; amino acids 111-125 of VH of
      human anti-factor VIII antibody B02C11 preceded by cyteine

<400> SEQUENCE: 11

```
Cys Ala Val Tyr Tyr Cys Ala Val Pro Asp Pro Asp Ala Phe Asp Ile
1               5                   10                  15
```

<210> SEQ ID NO 12
<211> LENGTH: 9
<212> TYPE: PRT
<213> ORGANISM: artificial sequence
<220> FEATURE:
<223> OTHER INFORMATION: synthetic peptide; amino acids 106-114 of VH
      (CDR3) of anti-Der p2 CD4+ T-cell clone G121

<400> SEQUENCE: 12

```
Val Tyr Phe Cys Ala Ser Ser Glu Arg
1               5
```

<210> SEQ ID NO 13
<211> LENGTH: 16
<212> TYPE: PRT
<213> ORGANISM: artificial sequence
<220> FEATURE:
<223> OTHER INFORMATION: synthetic peptide; amino acids 103-117 of VH of
      anti-Der p2 CD4+ T-cell clone G121 preceded by cysteine

<400> SEQUENCE: 13

```
Cys Gln Thr Ala Val Tyr Phe Cys Ala Ser Ser Glu Arg Thr Gly Gly
1               5                   10                  15
```

<210> SEQ ID NO 14
<211> LENGTH: 15
<212> TYPE: PRT
<213> ORGANISM: artificial sequence
<220> FEATURE:
<223> OTHER INFORMATION: synthetic peptide; amino acids 1541-1555 of ALK
      protein

<400> SEQUENCE: 14

```
Gly Ala Ala Glu Gly Gly Trp Thr Gly Pro Gly Ala Gly Pro Arg
1               5                   10                  15
```

<210> SEQ ID NO 15
<211> LENGTH: 12
<212> TYPE: PRT
<213> ORGANISM: artificial sequence
<220> FEATURE:

-continued

<223> OTHER INFORMATION: synthetic peptide; amino acids 1544-1555 of ALK
      protein preceded by cysteine

<400> SEQUENCE: 15

Cys Gly Gly Trp Thr Gly Pro Gly Ala Gly Pro Arg
1               5                   10